(12) United States Patent
Stupecky

(10) Patent No.: US 7,762,804 B1
(45) Date of Patent: Jul. 27, 2010

(54) BALLOON CATHETER FOLDING AND WRAPPING DEVICES AND METHODS

(75) Inventor: Josef J. Stupecky, Laguna Niguel, CA (US)

(73) Assignee: Interface Associates, Inc., Laguna Niguel, CA (US)

(*) Notice: Subject to any disclaimer, the term of this patent is extended or adjusted under 35 U.S.C. 154(b) by 1165 days.

(21) Appl. No.: 11/303,546

(22) Filed: Dec. 16, 2005

Related U.S. Application Data

(60) Provisional application No. 60/637,345, filed on Dec. 17, 2004.

(51) Int. Cl.
*B29C 53/08* (2006.01)

(52) U.S. Cl. .................. 425/392; 425/397; 425/402; 72/402

(58) Field of Classification Search .......... 425/383, 425/392–393, 409, 405.1; 72/402
See application file for complete search history.

(56) References Cited

U.S. PATENT DOCUMENTS 6,360,577 B2 * 3/2002 Austin .................. 72/402
6,988,881 B2    1/2006 Motsenbocker et al.
7,389,670 B1 * 6/2008 Kokish et al. .................. 72/402
7,448,243 B1 * 11/2008 Motsenbocker ................ 72/76

* cited by examiner

*Primary Examiner*—Richard Crispino
*Assistant Examiner*—Thu Khanh T Nguyen
(74) *Attorney, Agent, or Firm*—Knobbe, Martens, Olson & Bear, LLP

(57) ABSTRACT

A balloon folding apparatus is provided for use in the manufacture of balloon catheters. The balloon folding apparatus includes a plurality of arms and a plurality of blades attached to the plurality of arms such that the plurality of blades is capable of translating in a radial direction. Preferably, a plurality of stepper motors coupled to the plurality of arms provides precise radial movement of the plurality of blades. Each of the plurality of blades is profiled to create a plurality of folds in a balloon catheter. A balloon wrapping apparatus is also provided and operates in a similar manner. The balloon wrapping apparatus includes a plurality of blades configured to wrap a folded balloon catheter around a catheter shaft so as to minimize the diameter of the balloon catheter.

29 Claims, 14 Drawing Sheets

BALLOON CATHETER FOLDING AND WRAPPING DEVICES AND METHODS

CROSS-REFERENCE TO RELATED APPLICATIONS

This application claims priority under 35 U.S.C. §119(e) to U.S. Provisional Application Ser. No. 60/637,345 filed on Dec. 17, 2004, the entire content of which is hereby incorporated by reference.

BACKGROUND OF THE INVENTION

1. Field of the Invention

The present invention generally relates to balloon catheters. More particularly, the present invention relates to devices and methods used to fold and wrap balloon catheters during the manufacture of such balloon catheters.

2. Description of the Related Art

A balloon catheter generally comprises an inflatable balloon that is mounted along a distal end of an elongate catheter body (i.e., shaft). Balloon catheters are used by physicians in a wide variety of therapeutic procedures. In one common use, a folded balloon catheter is advanced through a blood vessel to a region that has become occluded by atherosclerotic plaque. The balloon is inflated to dilate the occluded region and thereby improve the flow of blood through the vessel. In another common use, an expandable stent is provided along the exterior of the balloon. The balloon is advanced to the treatment site and is then inflated to deploy the stent. The balloon is then deflated and the balloon catheter is withdrawn from the patient. The expanded stent remains in the blood vessel to provide support to the vessel wall.

SUMMARY OF THE INVENTION

Embodiments of the present invention disclosed herein provide improved devices and methods for folding and wrapping balloon catheters. The preferred embodiments facilitate the manufacture of balloon catheters while minimizing costs and providing a balloon catheter that expands in a reliable and predictable manner. Further, the preferred embodiments provide a modular unit that is capable of folding and wrapping balloon catheters of a variety of different sizes and shapes.

Balloon catheters are typically formed of a very thin, yet strong material. During manufacture, a balloon catheter is folded at a number of locations along its longitudinal axis. After the balloon is folded in a variety of locations, the folds are wrapped around the catheter to reduce the balloon to a constrained condition having a very small diameter. In the case wherein the balloon is used to deploy a stent, the stent is crimped onto the balloon after the folding step. The balloon is advanced through the blood vessel to a treatment site while in the constrained condition. The balloon is inflated by directing a fluid through a lumen in the catheter to pressurize the balloon. During inflation, the balloon unfolds, rather than stretches. Embodiments of the present invention enable a balloon catheter to radially expand in a very predictable manner.

In one embodiment of the present invention, an apparatus for folding (i.e., fluting) a balloon catheter is provided. The apparatus includes a base unit, a control unit coupled to the base unit, and a power source. A plurality of arms is coupled to the base unit and arranged in a radial pattern about a central axis. The plurality of arms can translate in a radial direction toward and away from the central axis by use of a plurality of motors attached to the power source. A plurality of blades can be attached to and detached from the plurality of arms such that the plurality of blades can engage a balloon catheter, disposed in a cavity defined by the plurality of blades, during the folding process. In addition, the apparatus includes a carriage coupled to the base unit and a mounting unit disposed on the carriage for holding a balloon catheter. The carriage and mounting unit can translate in a direction generally parallel to the central axis such that a balloon catheter is provided to the cavity so that the balloon catheter can subsequently be folded.

A method for folding a balloon catheter is also provided. Such method includes the steps of providing a device having a plurality of arms arranged in a radial pattern about a central axis and capable of translating in a radial direction, attaching a plurality of blades to such plurality of arms, placing a balloon catheter on a mounting unit coupled to a carriage, translating the carriage and the mounting unit in a direction generally parallel to the central axis so that the balloon catheter is located within a cavity, and inflating the balloon catheter. The next steps in such method include actuating a plurality of motors to cause the plurality of blades to move in a radial direction toward the balloon catheter, moving the plurality of blades so that each of the plurality of blades contacts the inflated balloon catheter, and finally creating a plurality of folds (i.e., flutes) on the outer surface of the inflated balloon catheter.

In another embodiment of the present balloon folding device, an apparatus for folding a balloon catheter includes a base unit and a plurality of arms coupled to the base unit. The plurality of arms is configured in a radial pattern about a central axis and can translate in a radial direction toward and away from the central axis. A plurality of blades is attached to the plurality of arms and can translate with the plurality of arms so as to engage a balloon catheter during the folding process. In this embodiment, a cavity is also provided which is defined by the convergence of the plurality of blades about the central axis and such cavity can receive a balloon catheter in order for the plurality of blades to fold such balloon catheter.

Other embodiments of the present invention provide an apparatus for wrapping a folded balloon catheter about a catheter shaft so as to minimize the diameter of the balloon catheter. One embodiment includes a base unit, a control unit coupled to the base unit, and a power source. A plurality of arms is attached to the base unit and arranged in a radial pattern about a central axis. The plurality of arms can translate in a radial direction toward and away from the central axis by use of a plurality of motors attached to the power source. In addition, a plurality of blades can be attached to and detached from the plurality of arms and can engage the balloon catheter during the wrapping process. A cavity defined by the plurality of blades receives a balloon catheter by way of a mounting unit coupled to a carriage. The mounting unit can translate in a direction generally parallel to the central axis for inserting the balloon catheter into the cavity defined by the plurality of blades.

A method for wrapping a folded balloon catheter about a catheter shaft includes the initial step of providing a device having a plurality of arms configured in a radial pattern and capable of translating in a radial direction. Such method also includes the steps of attaching a plurality of blades to the plurality of arms, placing a folded balloon catheter on a mounting unit of a carriage, translating the carriage and the mounting unit in a direction toward a cavity defined by the plurality of blades, and actuating a plurality of motors for causing the plurality of blades to contact the balloon catheter. A final step includes pressing the plurality of folds on the outer surface of the balloon catheter around a catheter shaft so that the folds become wrapped around the catheter shaft minimizing the diameter of the balloon catheter.

In another embodiment, an apparatus for wrapping a folded balloon catheter is provided. The apparatus includes a base unit and a plurality of arms coupled to the base unit and arranged in a radial pattern. The plurality of arms can translate in a radial direction toward and away from a central axis. A plurality of blades is connected to the plurality of arms for engaging a balloon catheter during the wrapping process. In addition, a cavity is defined by the convergence of the plurality of blades about the central axis and can receive a balloon catheter for wrapping such balloon catheter around a catheter shaft.

BRIEF DESCRIPTION OF THE DRAWINGS

These and other features, aspects, and advantages of the present invention will now be described in connection with preferred embodiments of the invention in reference to the accompanying drawings. The illustrated embodiments, however, are merely examples and are not intended to limit the invention. The drawings include the following fourteen figures.

DETAILED DESCRIPTION OF THE PREFERRED EMBODIMENTS

The balloon catheter folding and wrapping devices described herein are cost effective tools that are particularly well suited for manufacturers of balloon catheters. These improved devices substantially speed-up, simplify, and improve the balloon folding and wrapping processes. The balloon folding and wrapping devices described herein may be used with a wide variety of balloon catheter sizes and shapes. The balloon folding and wrapping devices are preferably provided as separate units. Each fixture is preferably controlled by an electronic control unit.

The balloon folding and wrapping fixtures each comprise a plurality of movable blades which are disposed around the balloon and extend and retract in a radial direction along a linear path. The movement of the blades in the balloon folding fixture creates the folds. The movement of the blades in the balloon wrapping fixture wraps the folds around a catheter shaft so as to provide a small diameter. In one embodiment, the blades of the balloon folding and wrapping fixtures include built-in electric heaters and thermocouples. These built-in heaters are advantageously heater cartridges insertable into the blades. An electronic temperature controller may be provided to accurately maintain the blade temperatures at a set value. When heated blades are used during folding, the balloon tends to retain its folded shape after being removed from the balloon folding fixture. The heated blades also heat set the folds during the wrapping process.

Advantageously, a large number of components in the folding fixture are identical to components in the wrapping fixture. The modular nature and high repeatability of parts provides an important advantage by driving down the cost of manufacture and repair of the balloon folding device and the balloon wrapping device. As a result, manufactured balloon catheters can be folded and wrapped in preparation for insertion in the human body at a lower cost than is available under typical folding and wrapping processes. Embodiments of the balloon folding and wrapping devices will now be described in more detail.

Figure 1:
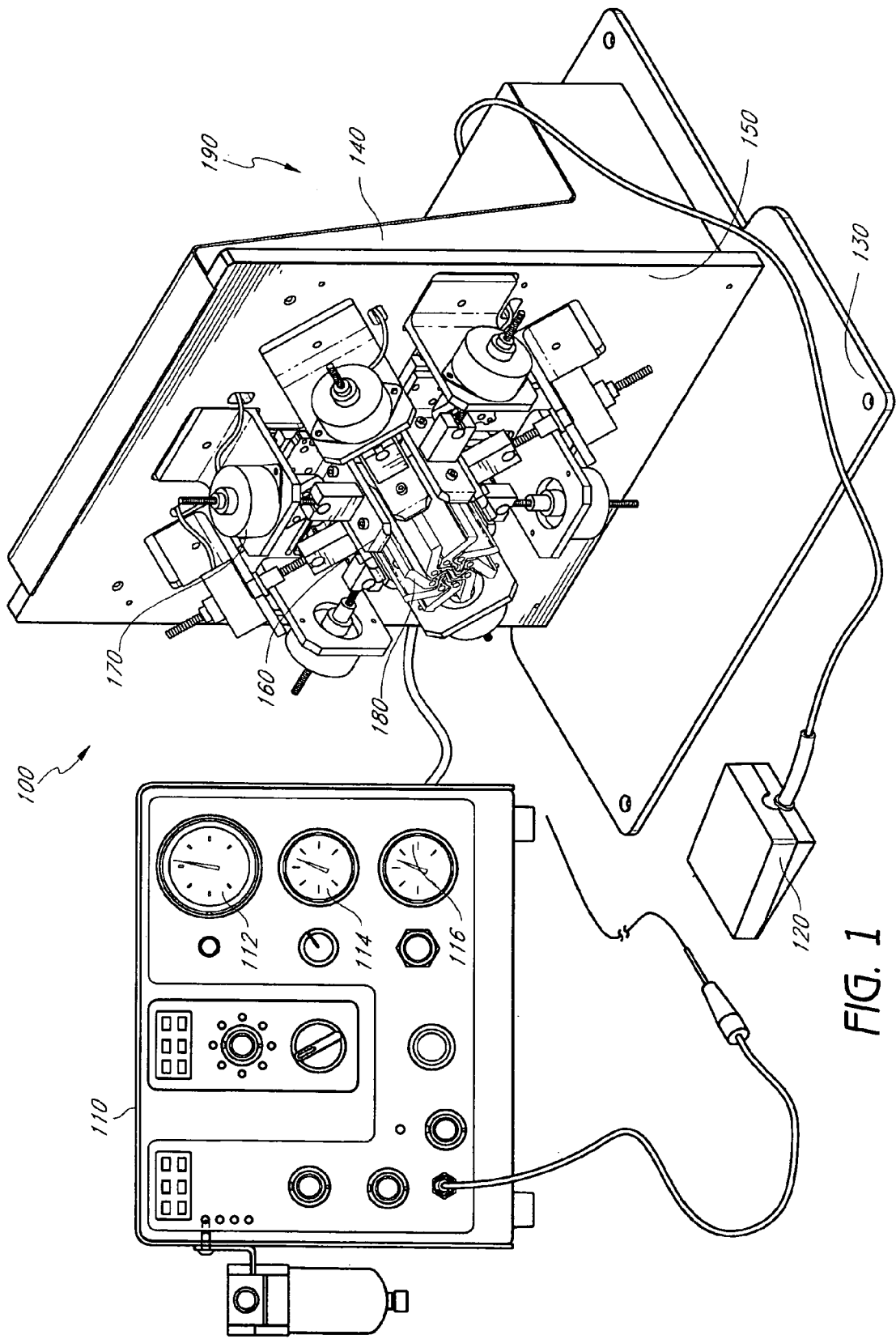
FIG. 1 is a perspective view of a balloon folding device in accordance with a preferred embodiment of the present invention.

As shown in FIG. 1, a balloon folding fixture 100 comprises a control unit 110 coupled to a base unit 190. The base unit 190 includes a base plate 130 upon which a support piece 140 is mounted thereon to provide support to a mounting face 150. The mounting face 150 contains a plurality of arms 160, a plurality of motors 170, and a plurality of blades 180. The plurality of blades 180 are coupled to the plurality of arms 160 and each of the plurality of blades 180 and the plurality of arms 160 is capable of translating in a radial direction by use of the plurality of motors 170. The plurality of motors 170 are coupled to the plurality of arms 160 and translation of each of the plurality of arms 160 and plurality of blades 180 is initiated by utilizing an actuator 120 that is coupled to the base unit 190. A balloon catheter is then inserted into a cavity formed by the plurality of blades 180.

In one embodiment, the balloon folding fixture 100 includes an electronic control unit 110 for controlling the inflation of a balloon catheter. The control unit 110 may include a pneumatic pump for applying a vacuum to the interior of the balloon, thereby causing the folded balloon to retain its shape after being folded.

The control unit 110 can include a motion control 112, a temperature control 114, and a pressure control 116. In addition, controls along the front panel of the control unit 110 may allow an operator to set one or more of the following parameters: (1) speed of the blade travel; (2) open cavity diameter in millimeters (maximum 9.5 mm on standard models, larger sizes optional) and closed cavity diameter in millimeters (minimum 0.7 mm on standard models, smaller sizes optional); (3) blade heating ON-OFF; (4) blade temperature, preferably from ambient to 125° C. (257° F.); (5) blade dwell time; (6) blade inflation pressure; (7) balloon folding pressure; and (8) balloon vacuum.

By way of specific example, in a preferred embodiment the open and closed cavity positions are selected with a resolution of 0.10 mm. To provide visual feedback, the magnitudes of individual parameters are preferably displayed on two digital readouts and three dial gauges. Additional LED control lights indicate the part of the cycle that the machine is currently executing and which blade temperature is displayed at that particular moment. For safety reasons, all moving parts of the balloon folding fixture are preferably covered by a clear polycarbonate shield (which is not shown in FIG. 1).

In one embodiment, the balloon folding fixture 100 is configured so that it can be used on a standard tabletop. The balloon folding device 100 is moderately sized so that it takes up a relatively small amount of space in a typical industrial setting. The balloon folding device 100, including the base unit 190 and the control unit 110, is portable and can easily be transferred from one location to another location. Advantageously, such relatively compact configuration and portability enable a user to utilize the balloon folding fixture 100 in a wide variety of locations and settings.

Figure 2:
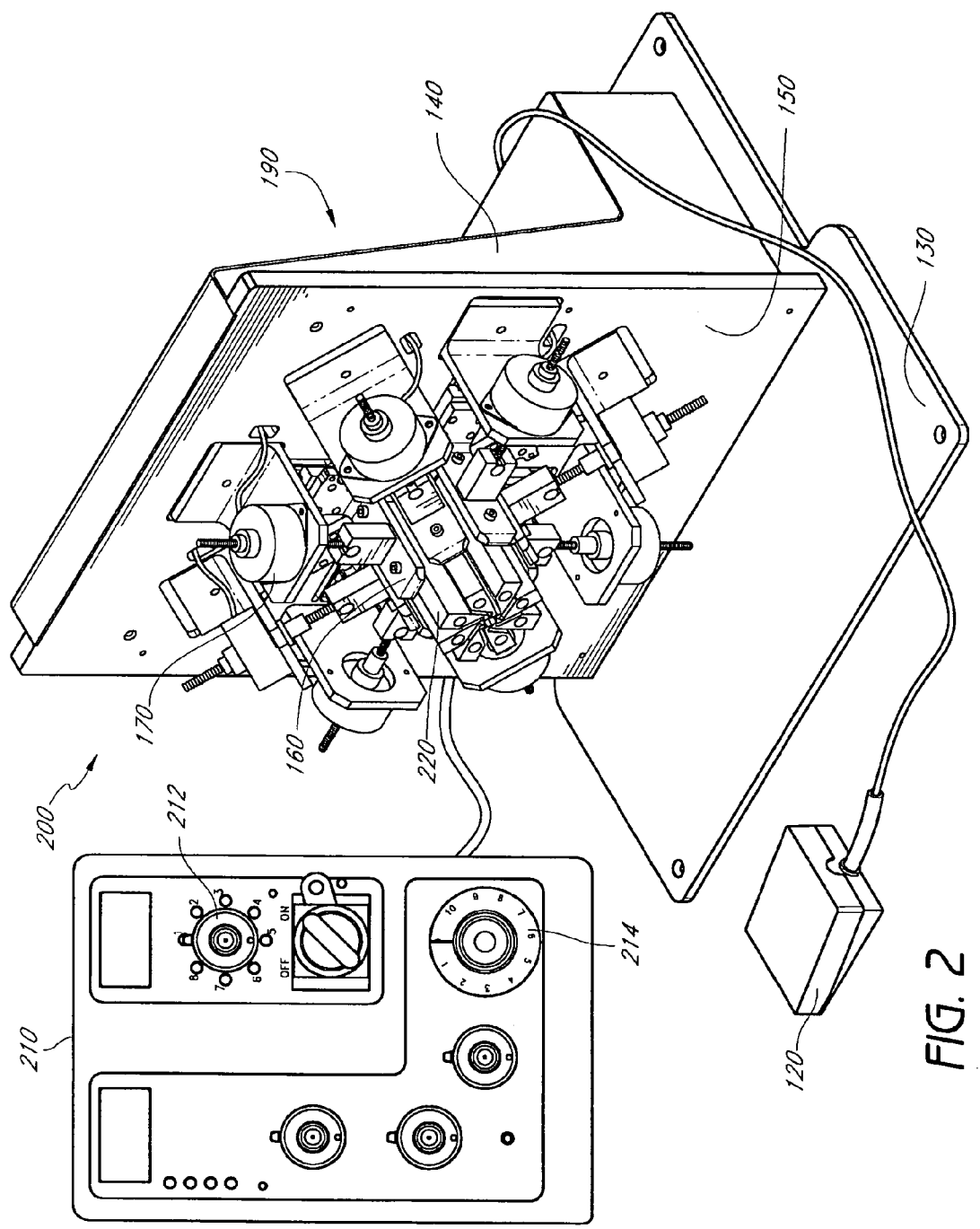
FIG. 2 is a perspective view of a balloon wrapping device in accordance with a preferred embodiment of the present invention.

FIG. 2 illustrates a balloon wrapping device 200. The balloon wrapping device 200 is substantially similar to the balloon folding device 100 as shown in FIG. 1. The balloon wrapping device 200 also includes a control unit 210 and a base unit 190. The base unit 190 includes a base plate 130 upon which a support piece 140 is mounted thereon to provide support to a mounting face 150. The mounting face 150 contains a plurality of arms 160, a plurality of motors 170, and a plurality of blades 220.

The plurality of blades 220 of the balloon wrapping device 200 are profiled differently from the plurality of blades 180 of the balloon folding device 100. For the folding device 100, the plurality of blades 180 are profiled so as to create a plurality of folds, also known in the art as flutes, in a balloon catheter. The tips of each of the plurality of profiled blades 180 are shaped into an interlocking profile having a concave surface that provide a plurality of slots for holding a plurality of flutes in a balloon catheter. As a result, a fan wheel shape composed of the plurality of flutes is imparted into the folded balloon catheter.

In the wrapping device 200, on the other hand, the plurality of blades 220 are profiled so as to wrap a folded balloon catheter around a catheter shaft so as to minimize the diameter of the balloon catheter. In particular, the tips of each of the plurality of profiled blades 220 are substantially flat and shaped so that the plurality of blades 220 forms a substantially octagonal configuration when in a retracted position. As the plurality of profiled blades 220 are translated radially inward, along a linear path, such an octagonal configuration becomes progressively smaller and will appear to form progressively smaller concentric circles. Advantageously, a balloon catheter with such a wrapped configuration can be inserted into a small cavity, such as within the human body, with greater effectiveness than a folded balloon catheter without a wrapped configuration.

This difference between the plurality of profiled blades 180 of the balloon folding device 100 and the plurality of blades 220 of the balloon wrapping device 200 is described in further detail below in connection with FIGS. 8 through 14. In particular, FIGS. 8 through 12 illustrate embodiments of a plurality of profiled blades 180 for a balloon folding device 100. On the other hand, FIGS. 13 and 14 illustrate embodiments of a plurality of profiled blades 220 for a balloon wrapping device having an eight blade configuration.

The plurality of blades 220 are coupled to the plurality of arms 160 and each of the plurality of blades 220 and the plurality of arms 160 is capable of translating in a radial direction by use of the plurality of motors 170. The plurality of motors 170 are coupled to the plurality of arms 160 and translation of each of the plurality of arms 160 and plurality of blades 220 is initiated by utilizing an actuator 120 that is coupled to the base unit 190. A folded balloon catheter can be inserted into a cavity formed by the plurality of blades 220.

In one embodiment, the plurality of blades 220 is mounted to linear guides comprising ball bearings. It has been found that the use of precision ball bearings allows for very precise blade movement. As a result, tight tolerances may be incorporated between each of the plurality of blades 220 for allowing the distal end portions of the blades to interlock without jamming. In another embodiment, each of the plurality of blades 220 has a built-in electric heater and thermocouple. The electric heater may comprise a removable heat cartridge. Each of the plurality of profiled blades 220 are advantageously formed from heat treated beryllium copper. Beryllium copper is preferred due to its excellent heat conduction, which minimizes temperature gradients along each of the plurality of blades 220. Accordingly, each of the plurality of blades 220 formed of beryllium copper provides greater consistency as compared, for example, with blades formed of stainless steel.

In one embodiment, the balloon wrapping fixture 200 comprises an electronic control unit 210. The control unit 210 can include a motion control 212 and a temperature control 214. It should be noted that the control unit 210 of the balloon wrapping fixture 200 preferably does not include a pressure control whereas the control unit 110 of the balloon folding fixture 100 does include a pressure control 116. This is so because the balloon wrapping fixture 200 operates so as to wrap a folded balloon catheter around a catheter shaft and does not typically apply pressure or a vacuum to the interior of the balloon catheter in this embodiment.

In addition, controls along the front panel of the control unit 210 may be provided for allowing the operator to set one or more of the following parameters: (1) speed of the blade travel; (2) open cavity diameter in millimeters (maximum 9.5 mm on standard models, larger sizes optional) and closed cavity diameter in millimeters (minimum 0.7 mm on standard models, smaller sizes optional); (3) blade heating ON-OFF; (4) blade temperature, preferably from ambient to 125° C. (257° F.); and (5) blade dwell time. In preferred embodiments, the open and closed cavity positions may be selected with a resolution of 0.10 mm. To provide visual feedback, the magnitudes of individual parameters are preferably displayed on two digital readouts and three dial gauges. Additional LED control lights indicate the part of the cycle that the machine is currently executing and which blade temperature is displayed at that particular moment. For safety reasons, all moving parts of the balloon wrapping fixture are preferably covered by a clear polycarbonate shield (which is not shown in FIG. 2).

In general terms, the balloon wrapping fixture preferably comprises two components linked by signal cables. The balloon wrapping fixture 200 includes a wrapping/crimping fixture and a wrapping fixture control unit 210 with LCD displays. In one preferred embodiment, the front panel controls allow the operator to set the maximum open cavity diameter to 9.5 mm and the minimum closed cavity diameter to 0.7 mm. Additional LED lights may be provided to indicate what part of the machine cycle is currently being executed as well as to provide a visual signal showing which blade temperature is being monitored at any given moment.

The balloon folding device 100, as shown in FIG. 1, and the balloon wrapping device 200, as shown in FIG. 2, are preferably constructed, at least in part, from precision machined aluminum components. The machined components are preferably hard anodized to enhance surface hardness, corrosion resistance, and appearance. The folding and wrapping blades may be machined by a wire EDM process from heat treated beryllium copper. This material offers an excellent combination of hardness and thermal conductivity. The folding and wrapping fixtures are configured for use with a wide variety of balloon types. For example, the fixtures are well suited for balloons made from materials such as nylon, PEBAX, polyurethane, and PET. However, the folding device 100 and the wrapping device 200 can be used with other balloon catheters as well.

One preferred embodiment of a balloon wrapping fixture 200 comprises an electrically operated tabletop unit which employs a plurality of radially arranged blades 220. Each of the blades includes a body portion and a tip portion. Precision stepper motor driven ball screws preferably control the motion and position of the blades with 0.00025 inch (0.0064 mm) resolution. The tips of the blades are preferably shaped in such a way that they form a cavity of an approximately circular cross section when the blades are retracted. When the blades are retracted, the cavity has a diameter of 0.1884 inches and is sized for receiving the folded balloon. When the blades move inwards toward the center, this cavity becomes progressively smaller until it collapses to a diameter of 0.03 inches. Cooperation of the blades provides a smooth and uninterrupted circumference of the cavity. As the cavity decreases in size, the balloon folds (i.e., flutes) are forced to curl around the catheter shaft in a substantially symmetrical manner. As the blades reach the end of their travel, the blades compress the folds along the catheter shaft. The blades may be held in the final position for a period of time (e.g., 10 seconds).

The blades can include heating elements. Application of heat facilitates heat setting the folded balloon in the final wrapped position. The blades then retract for removal of the folded and wrapped balloon. The tip geometry allows for progressive enlargement of the cavity when the blades start moving radially away from the center of the cavity.

The following lists the specifications for preferred embodiments of a balloon wrapping fixture: (1) balloon sizes of up to 20 mm×120 mm; (2) number of blades can include 3, 4, 5, 6 or 8; (3) heat setting temperature ranges from ambient to 125° C. (257° F.); (4) fixture size of 12.50" W×13.50" H×13.75" D (318 mm×343 mm×349 mm); (5) control unit size of 10.13" W×8.50" H×8.00" D (257 mm×216 mm×203 mm); (6) weight of wrapping fixture can be 9.0 to 18 lbs (4.0 to 8.2 kg); (7) control unit weight can be 8.0 lbs (3.6 kg); and (8) power requirements can range from 95 to 240 VAC, 50 to 60 Hz, 60 W.

A variety of alternative blade embodiments is illustrated for use with the balloon wrapping fixture. Several different sizes of blades are available both in terms of length and cavity diameters. The tip geometry allows for progressive reduction of the cavity diameter when the blades move radially inward toward the center of the cavity.

The general steps of folding and wrapping a balloon will now be described according to one preferred method of operation. First, the balloon folding parameters and the balloon inflation pressure/vacuum are selected by the operator on the front panel of the control unit 110 that comes with the balloon folding device 100. In order to set the open cavity position, the balloon is pressurized, preferably to approximately six or seven atmospheres, and the diameter is measured, such as with calipers. The control unit is then programmed such that the open cavity position is slightly larger than the diameter of the balloon to facilitate insertion of the balloon. The balloon catheter is then mounted and inserted into the balloon folding fixture. The blades are then actuated such that they move radially inward along a linear path to engage the outer surface of the balloon. The movement of the blades may be controlled by a switch, such as, for example, a footswitch. As the blades moves radially inward, the blades push inward along certain locations, thereby creating a plurality of longitudinal folds in the balloon. During movement of the blades, the pressurization mechanism switches to a back pressure regulator which allows air to escape the balloon as it is compressed, thereby maintaining a substantially constant pressure within the balloon.

The number of folds (i.e., flutes) in the balloon is equal to the number of blades and preferably varies from three to eight blades depending on the balloon size, balloon material, and balloon wall thickness. When the blades reach the end of their travel and the folds have been created, the pressurization mechanism then applies a negative pressure (i.e., a vacuum is applied) to withdraw the remaining air from the balloon and further set the flutes in place. The vacuum preferably stays on for the remaining steps of the process (e.g., wrapping, etc.). To still further hold the folded shape, the flutes are heat-set by heated blades to enhance material shape memory.

Applying pneumatic pressure to the balloon catheter can be performed by undertaking the following steps: (1) pressurizing the balloon in order to distend the balloon during insertion into the folding cavity; (2) maintaining a positive pressure at a set level while allowing air to escape from the balloon during folding; and (3) applying a vacuum to the folded balloon to hold the balloon in the folded shape before it is transferred to the wrapping fixture. The pneumatic pressure process can employ an optional air chuck and air clamp. An embodiment comprising an air chuck and air clamp is particularly well suited for fluting large spherical, un-mounted balloons. A similar pneumatic schematic without the air chuck and air clamp is better suited for use with an elongate balloon.

After the folding process is completed, the folded balloon is then removed from the fixture and is inserted into a central cavity of a balloon wrapping fixture 200. The balloon wrapping fixture 200 utilizes a variable orifice to tightly and uniformly wrap the balloon flutes around a catheter shaft in an efficient and predictable manner. If necessary, the balloon wrapping fixture 200 may also be used to crimp a stent onto the folded balloon. The balloon folding parameters as well as balloon inflation pressure/vacuum may be selected by the operator. For example, buttons or switches may be provided on the front panel of a control unit 210 that comes with each fixture. Embodiments can include customized versions available to handle other balloon sizes. The balloon wrapping fixture 200 is preferably provided separately from the fluting fixture 100 for enhanced modularity. The modularity allows the user to purchase only a single fixture (i.e., a fluting fixture or a wrapping fixture) without paying for features that may not be necessary, thereby providing substantial cost savings. For example, if only stent crimping is performed, the user may choose to purchase only the wrapping fixture. As a result, costs can be minimized by a particular user.

One preferred balloon wrapping fixture comprises eight interlocking wrapping blades. The starting diameter of the cavity is electronically adjusted to match the folded balloon envelope. To facilitate accurate insertion, the folded balloon is placed on a guiding V-block that is situated in front of the cavity. The V-block preferably travels on a ball bearing slide that guides the balloon into the cavity. Upon activation of a switch, miniature stepper motors begin advancing the wrapping blades radially inward along a linear path. For added efficiency, an actuator (e.g., footswitch) used to control the blades of the folding fixture may also be used to control the blades of the wrapping fixture.

As the octagon shaped cavity becomes progressively smaller, the balloon flutes are compressed inward and are forced to curl around the shaft in a symmetrical fashion. In one embodiment, the blades preferably compact the balloon with a radial force approaching 12 lbs (53.5 N). The end position of the blade travel is electronically set according to the catheter shaft diameter. The balloon re-folding characteristic is enhanced by a controlled heat input into the material during the wrapping process. After reaching the end of travel, the blades stay in full contact with the compacted balloon for a period of an adjustable dwell time (e.g., 10 seconds). At the end of the cycle the blades back off slightly so the wrapped balloon can be easily withdrawn from the cavity. It should be noted that, at any point in this process, the operator may turn the blade heating on or off, adjust the blade temperature from ambient to 125° C. (257° F.), and/or adjust the dwell time.

After being withdrawn from the cavity of the balloon wrapping fixture, the wrapped balloon profile is small and very smooth since there are no secondary creases. Furthermore, the wrapped flutes remain straight thus minimizing the possibility of material bunching during insertion into the sheath. To preserve and protect the folded balloon, a sheath can be placed on the balloon from either a proximal or a distal end by a simple sliding motion. Placement from the proximal end may be easier and can accommodate tighter fitting sheaths. However, this approach should advantageously be planned for early in the catheter assembly sequence and the sheath should advantageously be placed on the shaft prior to balloon attachment. In many cases, the placement of the sheath from the distal tip yields nearly identical results both in terms of balloon profile and ease of installation. In various preferred embodiments, the sheath is formed of polyethylene and/or Teflon.

Finally, in a last step, the catheter luer hub is disconnected from the vacuum source. In preferred methods of use, it has been found that the total cycle time ranges from 15 to 40 seconds, depending on the balloon type and size. It should be noted that a large number of components in the fluting fixture 100 are advantageously substantially similar to the components in the wrapping fixture 200. The modular nature and high repeatability of parts provides an important advantage by driving down the cost of manufacture and repair.

The figures which follow (i.e., FIGS. 3 through 14) describe the present invention and its components in terms of a balloon folding fixture 100. Since embodiments of the balloon folding fixture 100 are substantially similar to embodiments of the balloon wrapping fixture 200, the following figures discuss embodiments of the present invention primarily in terms of the balloon folding fixture 100. It should be appreciated, however, that these figures also show and describe features of a balloon wrapping fixture 200. As a result, the features shown in the following figures describe not only a balloon folding fixture 100 but also describe a balloon wrapping fixture 200 of the present invention.

Figure 3:
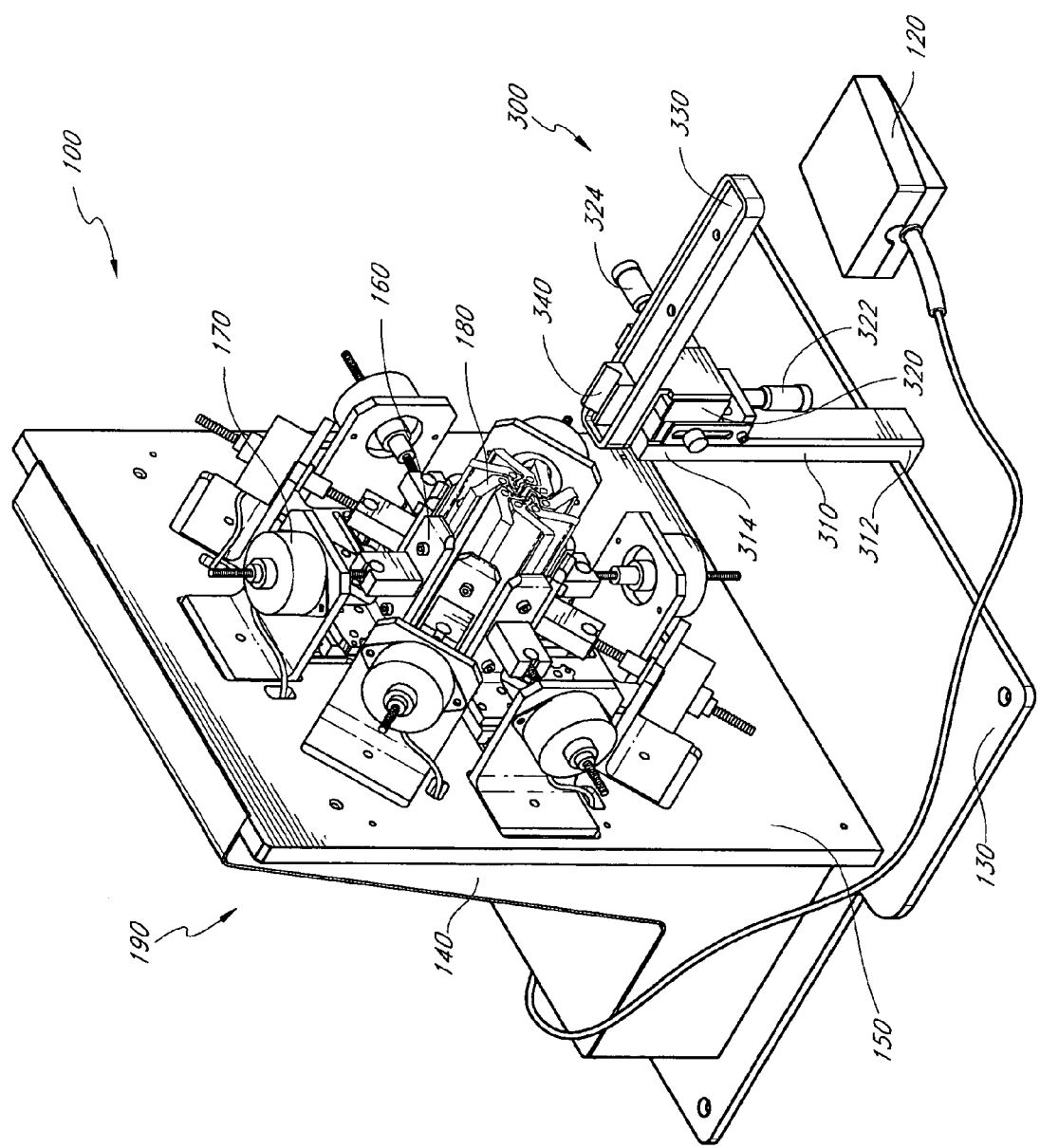
FIG. 3 is a perspective view of a base unit of the device including a balloon mounting feature for providing a balloon catheter to a plurality of blades of the balloon folding device as shown in FIG. 1.

FIG. 3 shows a perspective view of the balloon folding device 100 with a base unit 190 and a balloon mounting feature 300. The control unit 110 of the balloon folding device 100 is omitted from FIG. 3. The base unit 190 of FIG. 3 is substantially similar to the base unit 190 described above in connection with FIG. 1. With reference to FIG. 3, to facilitate an easy and accurate insertion of either a folded balloon or a folded balloon with a stent, a guide V-block is preferably situated in front of the cavity. This V-block preferably travels on a ball bearing slide and guides the catheter tip into the cavity. Precision X-Y stage with micrometer dials allow for alignment of the catheter centerline with the centerline of the cavity.

In one embodiment, the balloon mounting feature 300 is coupled to the base unit 190 and the balloon mounting feature 300 allows a balloon catheter to be inserted into a cavity formed by the plurality of blades 180. The balloon mounting feature 300 preferably includes a support column 310, a motion component 320, a carriage 330, and a mounting unit 340. The support column 310 comprises a lower portion 312 and an upper portion 314. In one embodiment, the lower portion 312 of the support column 310 is adjacent to at least a portion of the base plate 130 of the base unit 190. For example, the lower portion 312 may be attached to the underside of the base plate 130 by a suitable fastening mechanism such as a bolt, screw, or adhesive. In other embodiments the support column 310 may not be adjacent the base plate 130 and could be located at a distance away from the base plate 130 and/or the base unit 190. For example, the lower portion 312 of the support column 310 could be attached to a portion of a tabletop, or other workspace area, as opposed to being attached directly to the base unit 190.

In another embodiment, the carriage 330 of the balloon mounting feature 300 is coupled to at least a portion of the support column 310. The carriage 330 lies substantially orthogonal to the support column 310. The motion component 320 is positioned adjacent the junction of the support column 310 and the carriage 330, and preferably is positioned on the underside of the carriage 330. The motion component 320 includes at least a vertical adjustment knob 322 and a horizontal adjustment knob 324. The vertical adjustment knob 322 allows a user to raise and lower the carriage 330 so as to permit precise alignment of the balloon mounting feature 300 in relation to the cavity defined by the plurality of blades 180. The horizontal adjustment knob 324 permits a user translate the carriage 330 in a substantially horizontal direction so as to allow a balloon catheter mounted on the carriage 330 to be inserted into the cavity defined by the plurality of blades 180.

In one mode, the carriage 330 comprises a slight recess on the upper portion of the carriage 330 and a mounting unit 340 contained thereon. As shown in FIG. 3, the mounting unit 340 can be V-shaped. Advantageously, such V-shape configuration permits a balloon catheter to be disposed within such space defined by the V-shape configuration. As a result, a balloon catheter can be sufficiently provided to either the balloon folding device 100 or the balloon wrapping device 200 of the present invention. It should be noted that the mounting unit 140 is not limited to the V-shape configuration as shown in FIG. 3. In other embodiments, for example, the mounting unit 140 can be configured in a U-shape, can have a square cut-out, or can have a flat top portion with no cut-out. Like methods of providing a balloon catheter to the balloon folding device 100 can be employed.

Figure 4A:
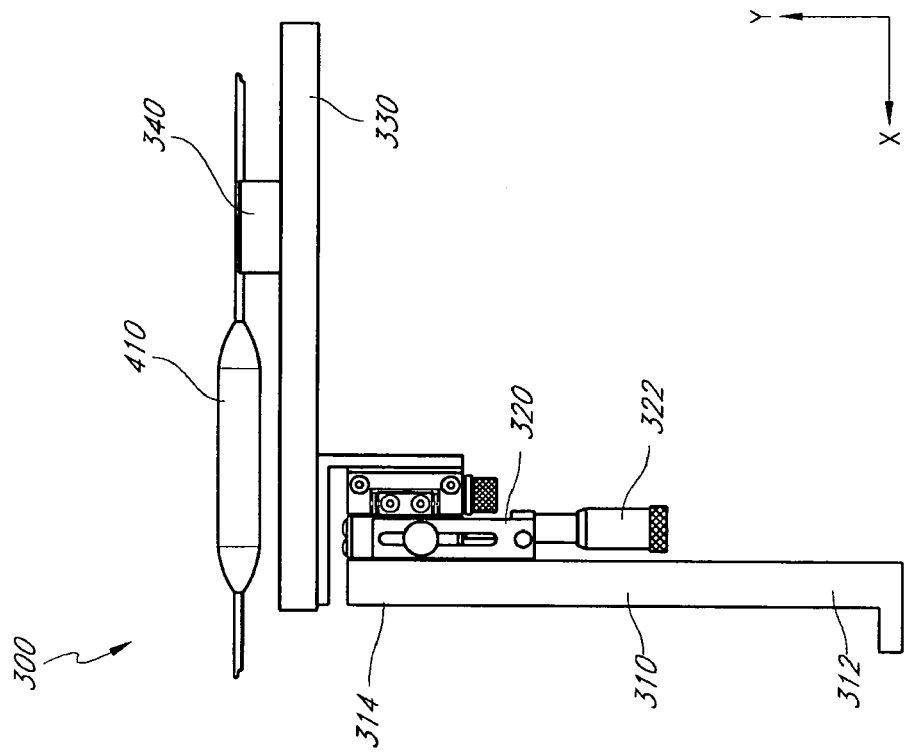
FIG. 4A is a side elevational view of the balloon mounting feature of the balloon folding device as shown in FIG. 3.
Figure 4B:
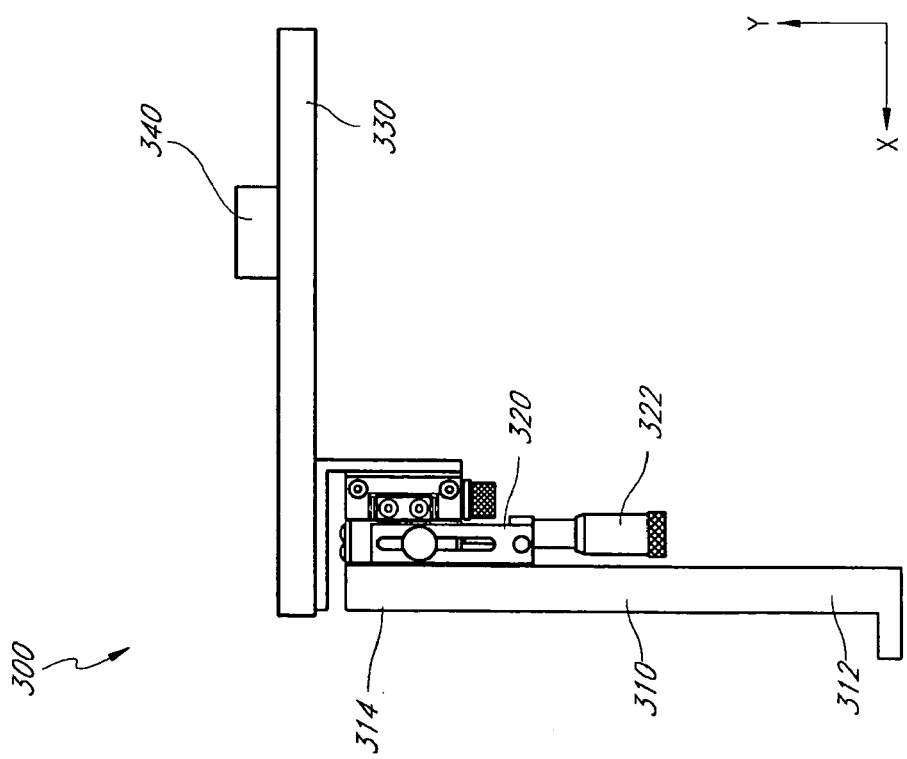
FIG. 4B is a side elevational view of the balloon mounting feature with a balloon catheter disposed on a carriage of the balloon mounting feature as shown in FIG. 4A.

FIGS. 4A and 4B show the balloon mounting apparatus 300 in further detail. FIG. 4A illustrates the balloon mounting apparatus 300 without a balloon catheter disposed on the mounting unit 340. The motion component 320 permits the carriage 330 to translate in a vertical direction Y and in a horizontal direction X. In particular, the vertical adjustment knob 322 facilitates linear movement of the carriage 330 in the direction Y. On the other hand, the horizontal adjustment knob 324 facilitates linear movement of the carriage 330 in the X direction. Such adjustment knobs 322, 324 permit a user to freely move the carriage 330 so as to position the balloon mounting feature 300 in a desired location relative to the balloon folding device, as shown in FIG. 1, or the balloon wrapping device, as shown in FIG. 2.

FIG. 4B illustrates the balloon mounting apparatus 300 with a balloon catheter 410 located on the mounting unit 340 of the carriage 330. The balloon catheter 410 fits within the V-shape recess in the mounting unit 340. Advantageously, the balloon catheter 410 can be inserted into a cavity of the balloon folding device 100 so as to permit creating folds in the exterior surface of the balloon catheter 410. In addition, the folded balloon catheter can be inserted into a cavity of the balloon wrapping device 100 so as to permit wrapping of the balloon catheter about a catheter shaft so as to minimize the diameter of the folded balloon catheter.

Figure 5:
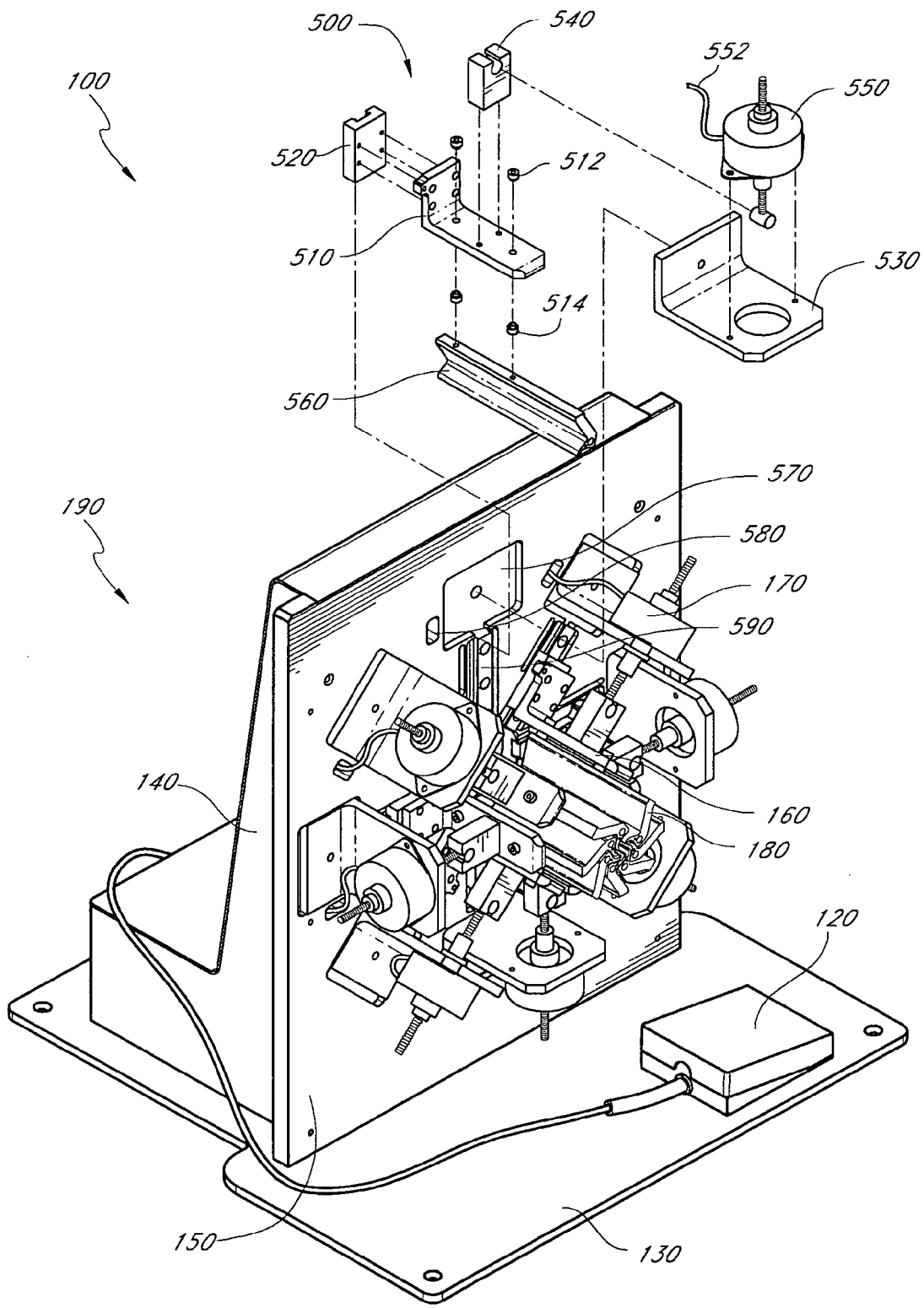
FIG. 5 is a partially exploded view of a base unit of the device showing an exploded arm assembly of the balloon folding device as shown in FIG. 1.

FIG. 5 shows an embodiment of the balloon folding device 100 with a partially exploded view of an arm assembly 500. The arm assembly 500 shows how the components of one of the plurality of arms 160 are situated with respect the mounting face 150 of the base unit 190. In one embodiment, each arm assembly 500 comprises a blade plate 510, an arm bracket 520, a motor bracket 530, a coupling piece 540, a motor 550, and a blade 560. The blade plate 510 is connected to a front face of the arm bracket 520. Upper fasteners 512 and lower fasteners 514 detachably connect the blade 560 to the blade plate 510. Advantageously, the blade 560 can be detached from the blade plate 510 so as to permit different blades having different size and configurations to be attached to the blade plate 510. As a result, a particular balloon folding device 100 can employ a variety of blade sizes and shapes so as to permit folding a variety of balloon sizes and shapes.

With reference to FIG. 5, the coupling piece 540 is attached to the blade plate 510 and is capable of mating with a portion of the motor 550. As a result, the coupling piece 540 connects the motor 550 to the blade plate 510 of the arm assembly 500. The motor 550 is further connected to the motor bracket 530. In one embodiment, the motor bracket 530 comprises a back side that is substantially orthogonal to a bottom side of the motor bracket 530. As such, the motor bracket 530 can fit substantially within a motor bracket recess 570 contained on the mounting face 150 of the base unit 190. The motor 550 also has a wire 552 that electrically couples the motor 550 to an external power source. The mounting face 150 of the base unit 190 contains an opening 580 that allows the wire to be placed through such opening 580 so that the wire can contact an external power source and not interfere with the operations of the balloon folding device 100.

As described in the preceding paragraph, in one embodiment, the motor bracket 530 can attach to the mounting face 150 via a motor bracket recess 570. In addition, the arm bracket 520 is configured to mate with a translation strip 590 disposed on the mounting face 150 of the base unit 190. Such translation strip 590 permits the arm assembly 500 to translate in a radial direction. As a result, the arm assembly can translate so as to make a cavity defined by the plurality of arms 160 and the plurality of blades 180 larger or smaller depending on the needs of the user. For example, the cavity will preferably be relatively large at one step in the balloon folding process so as to permit a balloon catheter to be inserted into the cavity. The cavity will preferably be relatively small at another step in the folding process such as when the plurality of blades 180 engage the balloon catheter and create folds on the surface thereof.

Figure 6:
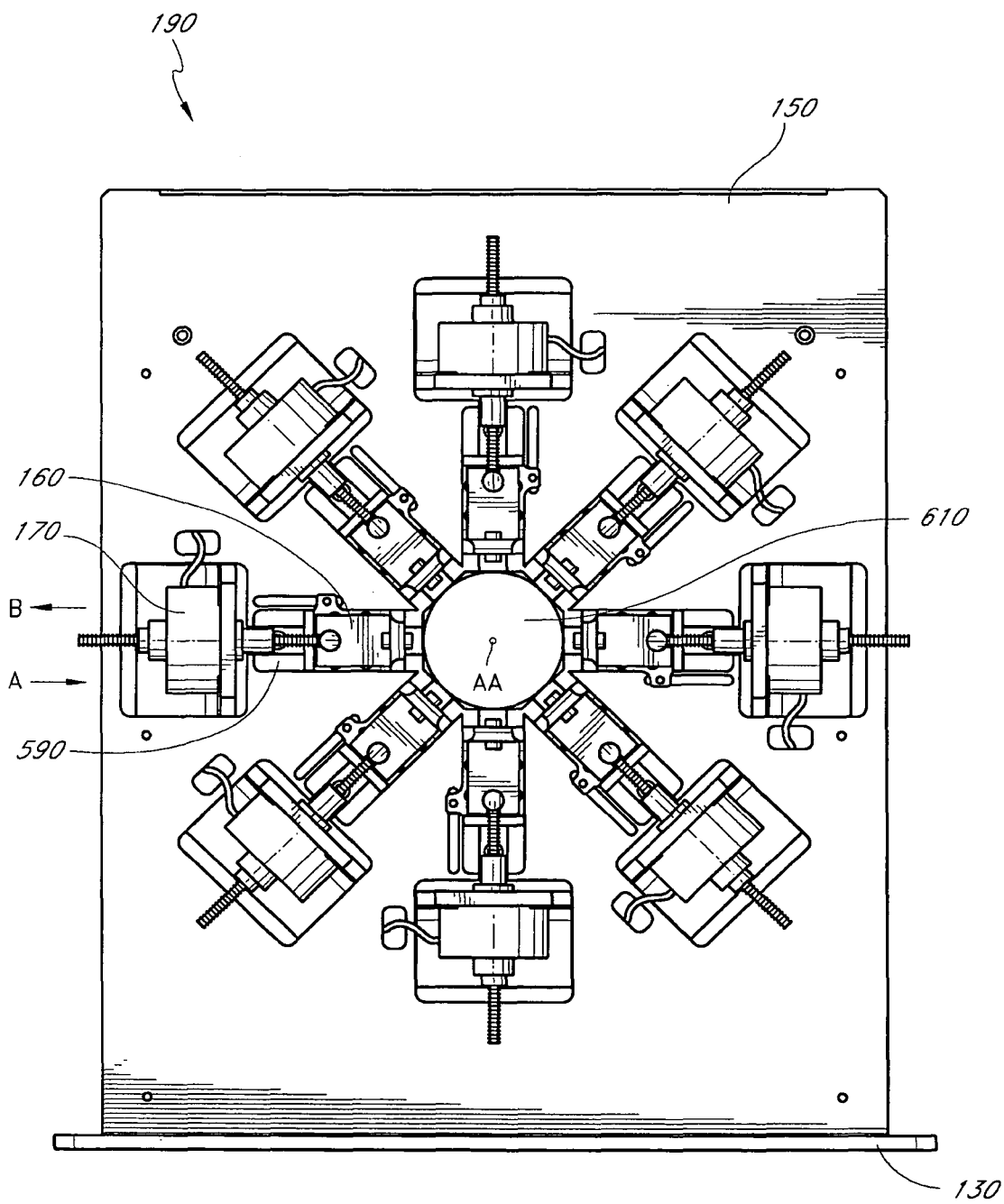
FIG. 6 is a front elevational view of a base unit of the device showing a plurality of arms disposed about a central axis AA such that each of the plurality of arms is capable of translating toward the central axis AA in a direction A and away from the central axis AA in a direction B.

FIG. 6 shows a front elevational view of the base unit 190 of the balloon folding device 100. FIG. 6 includes a plurality of arms 160 and a plurality of motors 170 at least partially coupled to the mounting face 150 of the base unit 190. As shown in FIG. 6, the plurality of arms 160 and the plurality of motors 170 comprise eight arms and eight motors, respectively. Other embodiments, for example, may comprise three arms and three motors, four arms and four motors, five arms and five motors, six arms and six motors, or any other suitable number of arms and motors.

In one embodiment, the plurality of arms 160 are arranged symmetrically about a central axis AA. Each of the plurality of arms 160 is capable of translating in a radial direction toward the central axis AA, which is shown as direction A in FIG. 6. In addition, each of the plurality of arms 160 is also capable of translating in a radial direction away from the central axis AA, which is shown as direction B in FIG. 6. A plurality of translation strips 590, which connect each of the plurality of arms 170 to the mounting face 150 of the base unit 190, facilitates radial translation of each of the plurality of arms 160 relative to the mounting face 150. Accordingly, the diameter of an opening 610 defined by the plurality of arms 160 can be increased or decreased by translating each of the plurality of arms 160 toward or away from the central axis AA. In particular, translating each of the plurality of arms 160 in direction A toward the central axis AA will decrease the diameter of the opening 610. Similarly, translating each of the plurality of arms 160 in direction B away from the central axis AA will increase the diameter of the opening 610.

In another embodiment, the plurality of motors 170 coupled to the plurality of arms 160 provides for precise radial movement. Preferably, the plurality of motors 170 comprises a plurality of stepper motors capable of moving the plurality of arms 160 in an incremental fashion with a high degree of precision. As a result, a user can create an opening that is precisely configured to receive, fold, and/or wrap balloon catheters of varying sizes and shapes. Advantageously, this permits the balloon folding device 100 and the balloon wrapping device 200 to be used to fold and wrap balloon catheters of a variety of sizes and shapes.

Figure 7:
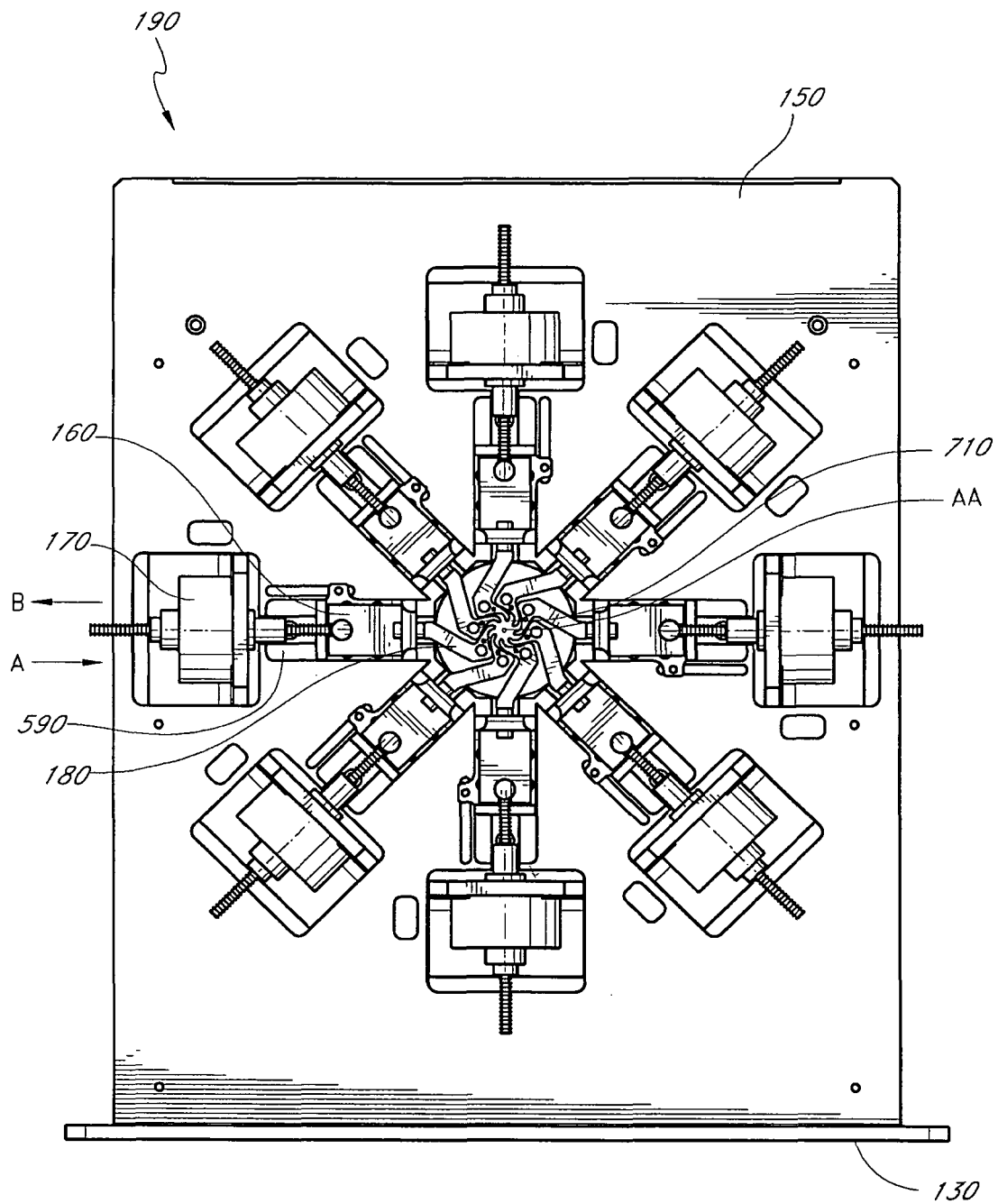
FIG. 7 is a front elevational view of a base unit of the device showing a plurality of arms and a plurality of blades disposed about a central axis AA such that each of the plurality of arms and each of the plurality of blades is capable of translating toward the central axis AA in a direction A and away from the central axis AA in a direction B.

FIG. 7 shows a front elevational view of the base unit 190 of the balloon folding device 100 with a plurality of blades 170 attached to the plurality of arms 160. As described in connection with FIG. 6, the plurality of arms 160 is capable of translating in a direction A toward a central axis AA and in a direction B away from the central axis AA. With the plurality of blades 180 attached to the plurality of arms 160, an opening 710 as shown in FIG. 7 is smaller than the opening 610 as shown in FIG. 6. The opening 710 can be configured so as to be capable of receiving a balloon catheter for either folding or wrapping such balloon catheter. As can be seen in FIG. 7, the opening 710 is relatively small and therefore the plurality of arms 160 and the plurality of blades 180 need only translate a relatively short distance in order to sufficiently fold a balloon catheter or wrap such folds around a catheter shaft. Accordingly, the precise radial movement provided by the plurality of motors 170, preferably a plurality of stepper motors, permits the plurality of blades 180 to engage the balloon catheter and wrap or fold such catheter with a very high degree of precision.

Figure 8A:
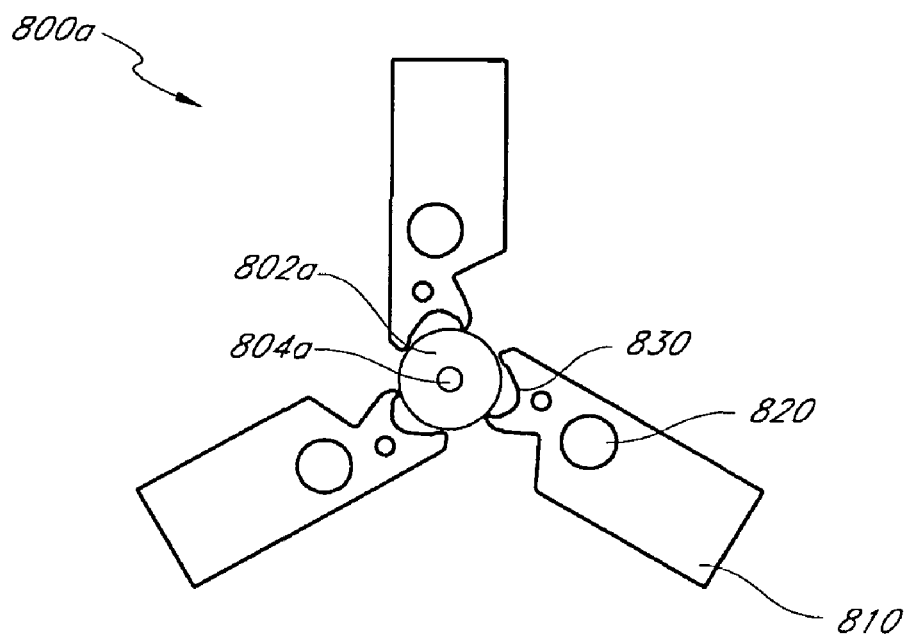
FIG. 8A is a front elevational view of a three blade configuration shown in an open position about a balloon catheter of the balloon folding device as shown in FIG. 1.
Figure 8B:
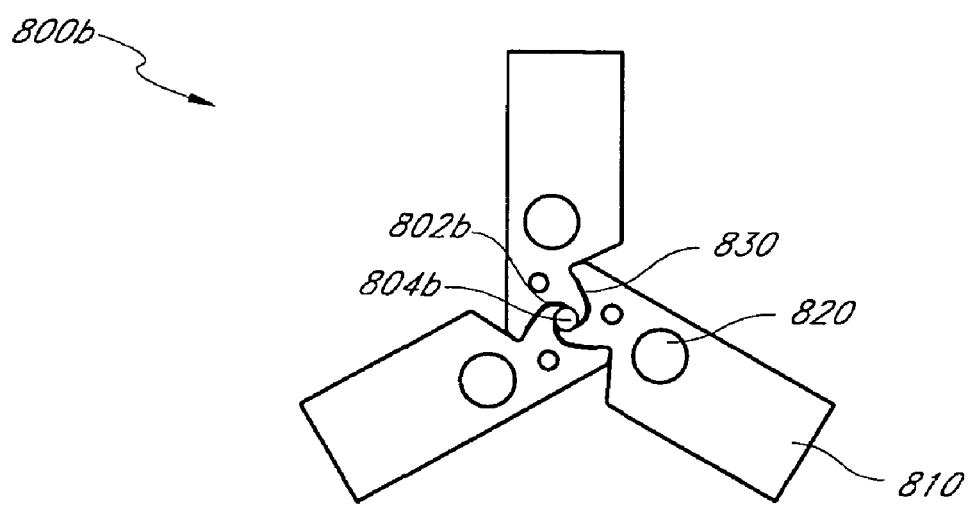
FIG. 8B is a front elevational view of a three blade configuration shown in a closed position creating three folds in a balloon catheter.

With reference to FIGS. 8A and 8B, one preferred set of blades is shown for use with the balloon folding fixture 100 comprising three profiled blades. The three blades extend and retract uniformly in a radial direction to create three folds (i.e., flutes) in the balloon. Each blade has a body portion 810 and a profiled tip 830 configured for forming a longitudinal fold in the balloon as the blade moves radially inward. An opening 820 in the body portion 810 of each blade allows the blade to be attached to and removed from at least a portion of the balloon folding device 100. It can be seen that the blades are shaped with a particular geometry which advantageously allows the blades to extend inward in a linear direction for creating the flutes. The shape of the profiled tip 830 allows each of the blades to extend inwardly without interfering with the other blades. The blades also cooperate to direct the resulting fold (i.e., flute) to one side such that it can then be easily wrapped around the catheter.

With reference to FIG. 8B, the set of blades is shown in the extended (i.e., closed) position 800b. It can be best seen in FIG. 8B that the blade tips 830 are shaped into an advantageous interlocking profile that provides three slots for holding the three flutes of the balloon and thereby imparting a fan wheel shape on the folded balloon.

As shown in FIGS. 8A and 8B, the profiled tip 830 of each of the blades has at least a partially concave surface relative to the balloon catheter 802a and the catheter shaft 804a. The partially concave surface on a profiled tip 830 of a particular blade is capable of substantially mating with a partially convex surface of the body portion 810 of an adjacent blade. However, there is preferably a slight gap between the concave surface of the profiled tip 830 of a particular blade and the convex surface of the body portion 810 of an adjacent blade. Such a gap provides an area for a particular flute to be created in the balloon catheter during the balloon folding process. The size of the gap between adjacent blades varies; however, in one embodiment the gap is approximately 0.012 inches wide so as to house an exemplary balloon catheter flute. As shown in FIG. 8B, a plurality of flutes 802b is created as the plurality of blades translate radially inward toward a catheter shaft 804b and, therefore, the balloon catheter is folded.

Each of the blades preferably moves radially inward along a linear track during the folding process. More particularly, the blades may be attached to ball bearing slides that provide precision guidance with little or no play. In the embodiment shown in FIGS. 8A and 8B, when in the fully retracted (i.e., open) position 800a, the set of blades forms a cavity capable of receiving a balloon catheter 802a having a diameter of approximately 0.24 inches (5.99 mm). When in the extended (i.e., closed) position 800b, the diameter of the cavity is reduced to correspond with a catheter shaft 804b having a diameter of approximately 0.055 inches (1.40 mm). Other embodiments of the three blade fluting configuration may be dimensioned differently so as to permit the folding of either larger or smaller manufactured balloon catheters.

In another embodiment, the three blade fluting fixture is capable of receiving a balloon catheter 802a having a diameter of approximately 0.177 inches (4.50 mm) and folding such balloon catheter 802a about a catheter shaft 804a having a diameter of approximately 0.040 inches (1.02 mm). In yet another embodiment, the three blade fluting fixture can receive a larger balloon catheter 802a having a diameter of approximately 0.315 inches (8.00 mm) and folding such balloon catheter 802a about a catheter shaft 804a having a diameter of approximately 0.070 inches (1.78 mm). Altering the shape of the body portion 810 and the tip 830 of each of the plurality of blades in the preceding embodiment, can allow folding such balloon catheter 802a (i.e., 0.315 inch diameter) about a catheter shaft 804a having a diameter of approximately 0.055 inches (1.40 mm).

Stepper motors are preferably provided for precisely controlling the movement of the blades. The stepper motors preferably control ball screws which are capable of controlling the position of the blades to within 0.001 inches (0.025 mm). The stepper motors may use optical sensors for improved alignment. During use, the balloon can be folded with high consistency and uniformity in less than five seconds. It will be appreciated by those skilled in the art that the present balloon folding fixture provides a substantial improvement over existing folding fixtures which use relatively complex and expensive pivoting blade mechanisms. In one preferred embodiment, the present folding fixture takes advantage of precision ball bearings for allowing very tight tolerances between the movable blades. The tight tolerance and precise movement allows the blades to move in a linear manner while providing excellent reliability.

The particular set of blades shown in FIGS. 8A and 8B is configured to create three longitudinal folds in the balloon. However, in alternative configurations, the number of blades may vary to create a different number of flutes. For example, in various alternative embodiments, the balloon can be folded into three, four, five, six or eight flutes. The folding blades may be provided with different lengths for accommodating balloons of different sizes. For example, the present invention may be used with balloons having lengths ranging from approximately 1 cm to 14 cm long. Preferred folding blades can handle balloons having diameters from approximately 1.5 mm to 20 mm. It should be appreciated that several different sizes of blades are available both in terms of length, number of flutes, and the catheter shaft diameter.

Preferably, the balloon folding fixture is equipped with heated blades. Using heated blades, the folded balloon is heat-set and a vacuum is applied to lock the folds in place. As shown in FIGS. 8A and 8B, each blade may be formed with an opening 820 or other receptacle for receiving a heating unit.

Figure 9A:
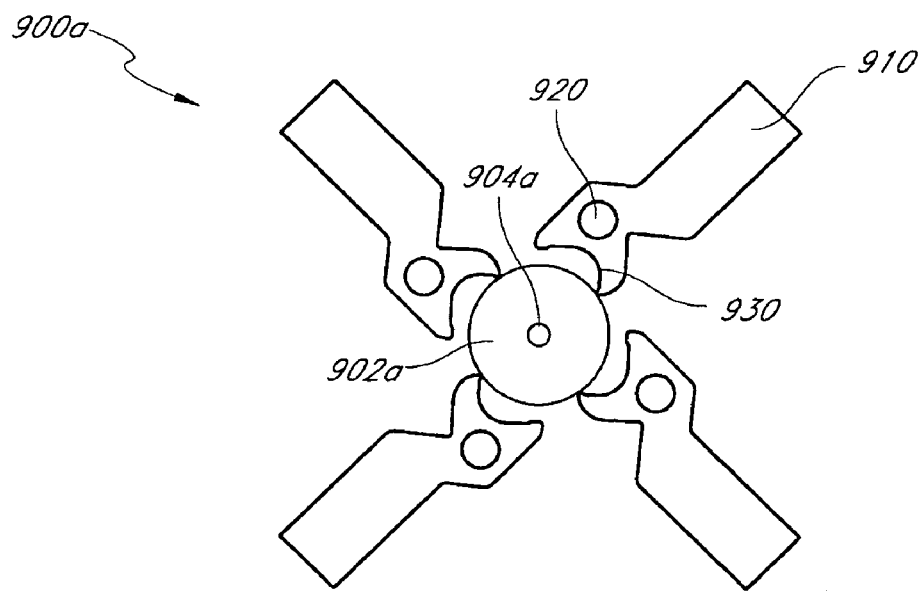
FIG. 9A is a front elevational view of a four blade configuration shown in an open position about a balloon catheter of the balloon folding device as shown in FIG. 1.
Figure 9B:
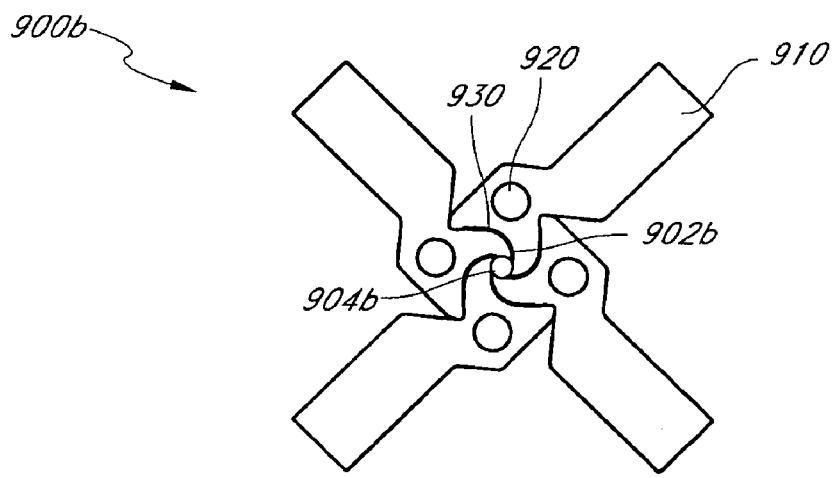
FIG. 9B is a front elevational view of a four blade configuration shown in a closed position creating four folds in a balloon catheter.

FIG. 9A illustrates a four blade embodiment with the blades in an open position 900a. Similar to the previously described embodiments, each blade has a body portion 910, a profiled tip portion 930, and an opening 920 in the body portion 910 of the blade. FIG. 9B shows the four blade embodiment in a closed position 900b so as to create four folds in a balloon catheter.

The profiled tip 930 of each of the four blades has at least a partially concave surface relative to the balloon catheter 902a and the catheter shaft 904a. The partially concave surface on a profiled tip 930 of a particular blade is capable of substantially mating with a partially convex surface of the body portion 910 of an adjacent blade. However, there is preferably a slight gap between the concave surface of the profiled tip 930 of a particular blade and the convex surface of the body portion 910 of an adjacent blade. Such a gap provides an area for a particular flute to be created in the balloon catheter during the balloon folding process. The size of the gap between adjacent blades varies; however, in one embodiment the gap is approximately 0.012 inches wide so as to house an exemplary balloon catheter flute. As shown in FIG. 9B, four flutes 902b are created as the four blades translate radially inward toward a catheter shaft 904b and, therefore, the balloon catheter is folded.

In one embodiment of the four blade configuration, the device is capable of receiving a balloon catheter 902a having a diameter ranging from approximately 3.0 mm to 12.0 mm. When in the closed position, as shown in FIG. 9B, the four blade device preferably folds the balloon catheter 902a about a catheter shaft having a diameter ranging from 0.075 inches to 0.100 inches so as to create four flutes 902b in the manufactured balloon catheter 902a. However, the four blade configuration is not limited to this particular embodiment and may include profiled blades of a variety of sizes and shapes so as to be capable of receiving a variety of sizes and shapes of balloon catheters and catheter shafts.

Figure 10A:
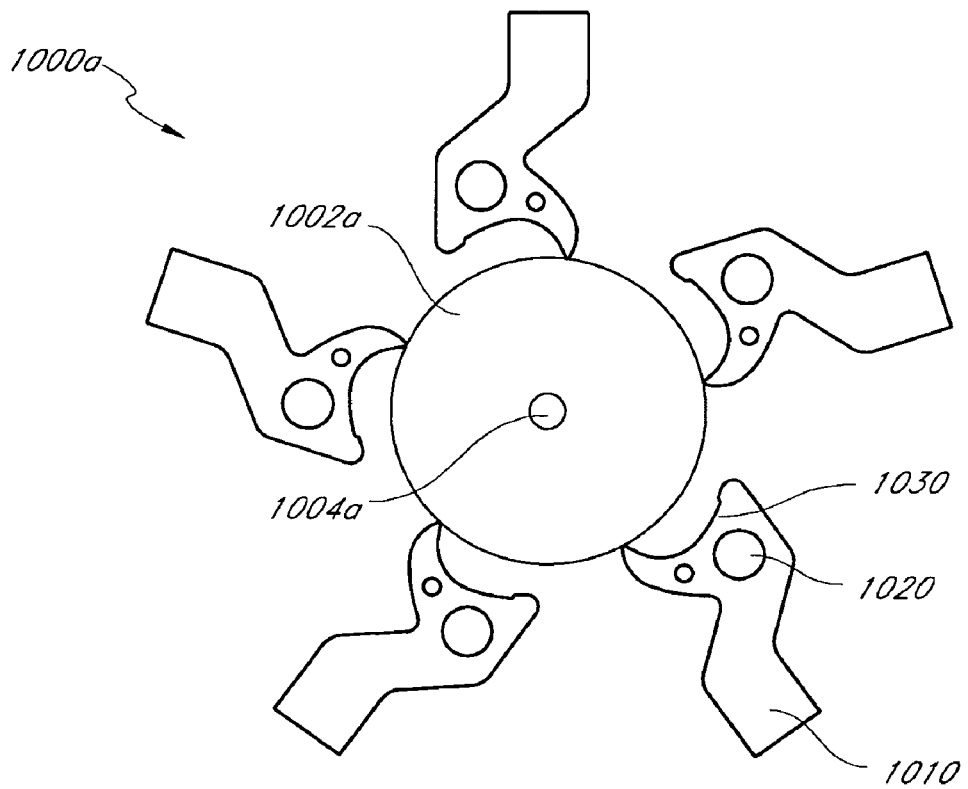
FIG. 10A is a front elevational view of a five blade configuration shown in an open position about a balloon catheter of the balloon folding device as shown in FIG. 1.
Figure 10B:
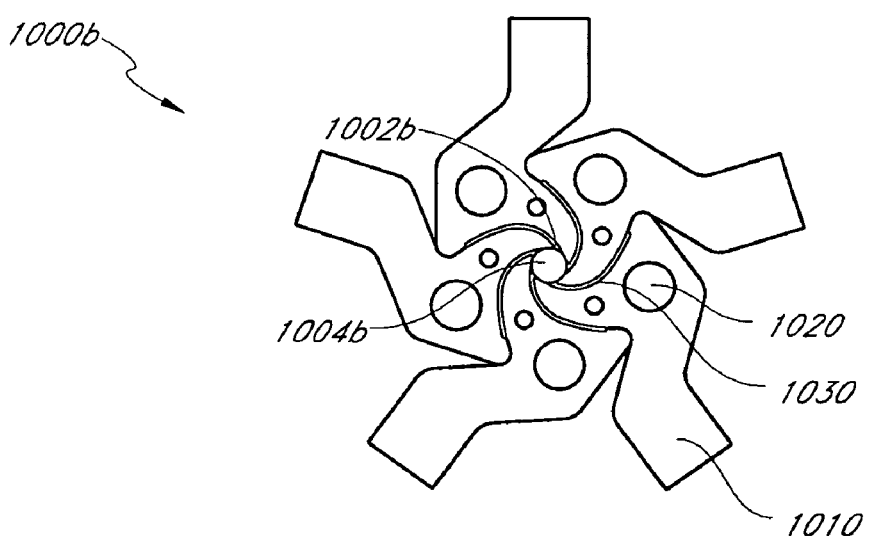
FIG. 10B is a front elevational view of a five blade configuration shown in a closed position creating five folds in a balloon catheter.

FIG. 10A illustrates a five blade embodiment with the blades in an open position 1000a. Similar to the previously described embodiments, each blade has a body portion 1010, a profiled tip portion 1030, and an opening 1020 in the body portion 1010 of the blade. FIG. 10B shows the five blade embodiment in a closed position 1000b so as to create five folds in a balloon catheter.

Similar to the three blade and four blade embodiments described above in connection with FIGS. 8 and 9, respectively, the five blade embodiment has blades having profiled tips 1030 having at least partially concave surfaces so as to substantially mate with partially convex surfaces of the body portions 1010 leaving five slight gaps for housing five flutes during the balloon catheter folding process.

In the embodiment shown in FIGS. 10A and 10B, the five blade device is capable of receiving a balloon catheter 1002a having a diameter of approximately 0.79 inches (19.99 mm) and folding such balloon catheter 1002a about a catheter shaft 1004b having a diameter ranging from approximately 0.090 inches to 0.100 inches. However, the five blade configuration is not limited to this particular embodiment and may include profiled blades of a variety of sizes and shapes so as to be capable of receiving a variety of sizes and shapes of balloon catheters and catheter shafts.

Figure 11A:
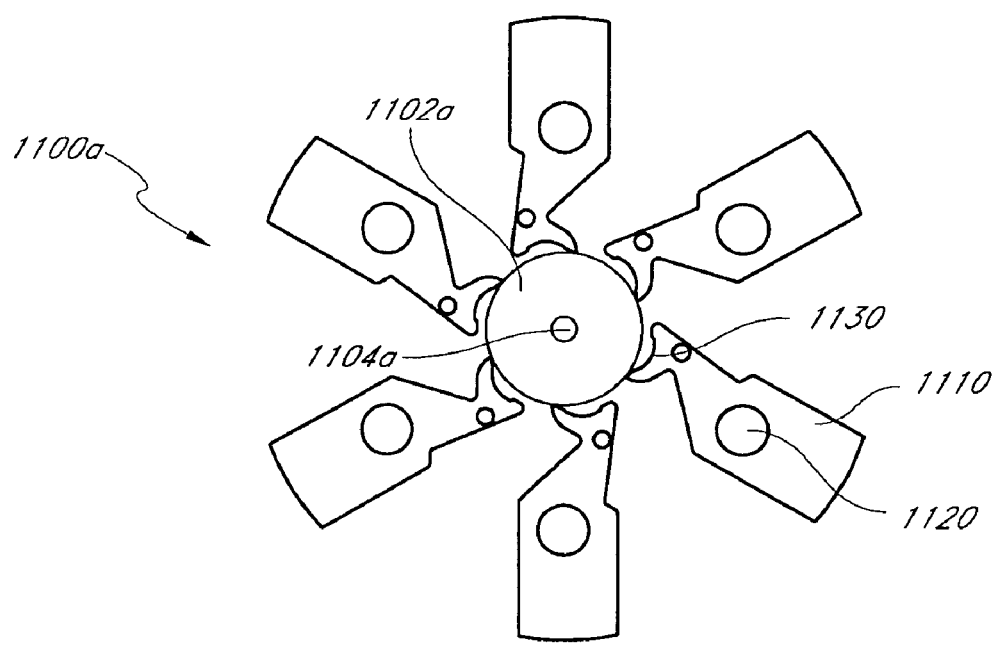
FIG. 11A is a front elevational view of a six blade configuration shown in an open position about a balloon catheter of the balloon folding device as shown in FIG. 1.
Figure 11B:
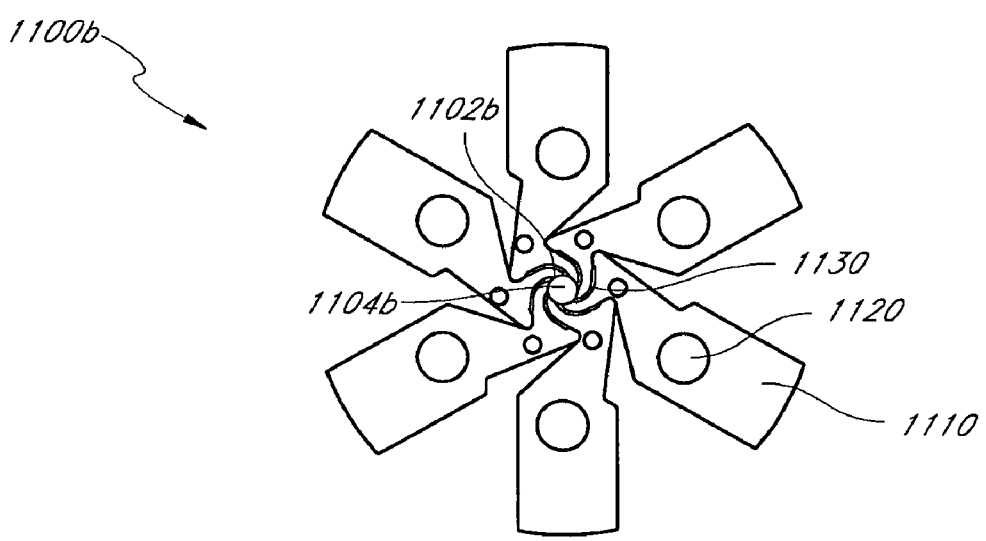
FIG. 11B is a front elevational view of a six blade configuration shown in a closed position creating six folds in a balloon catheter.

FIG. 11A illustrates a six blade embodiment with the blades in an open position 1100a. Similar to the previously described embodiments, each blade has a body portion 1110, a profiled tip portion 1130, and an opening 1120 in the body portion 1110 of the blade. FIG. 11B shows the six blade embodiment in a closed position 1100b so as to create six folds in a balloon catheter.

Similar to the embodiments described above, the six blade embodiment has blades having profiled tips 1130 having at least partially concave surfaces so as to substantially mate with partially convex surfaces of the body portions 1110 leaving six slight gaps for housing six flutes during the balloon catheter folding process.

In the embodiment shown in FIGS. 11A and 11B, the six blade device is capable of receiving a balloon catheter 1102a having a diameter of approximately 0.39 inches (10.01 mm) and folding such balloon catheter 1102a about a catheter shaft 1104b having a diameter ranging from approximately 0.075 inches to 0.090 inches. However, the six blade configuration is not limited to this particular embodiment and may include profiled blades of a variety of sizes and shapes so as to be capable of receiving a variety of sizes and shapes of balloon catheters and catheter shafts.

Figure 12A:
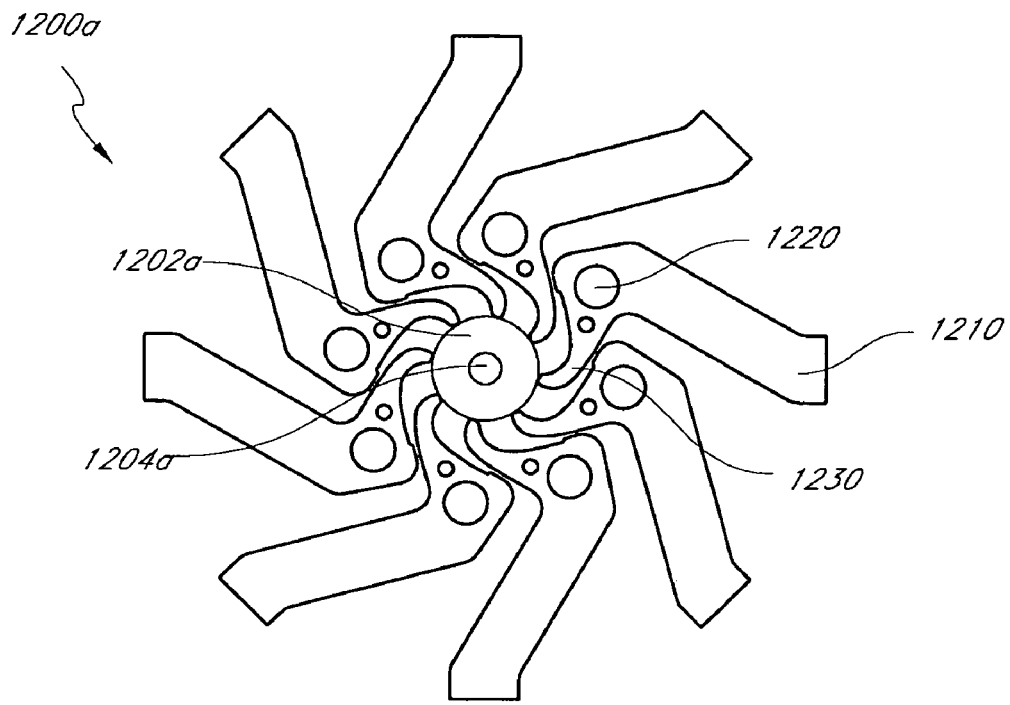
FIG. 12A is a front elevational view of an eight blade configuration shown in an open position about a balloon catheter of the balloon folding device as shown in FIG. 1.
Figure 12B:
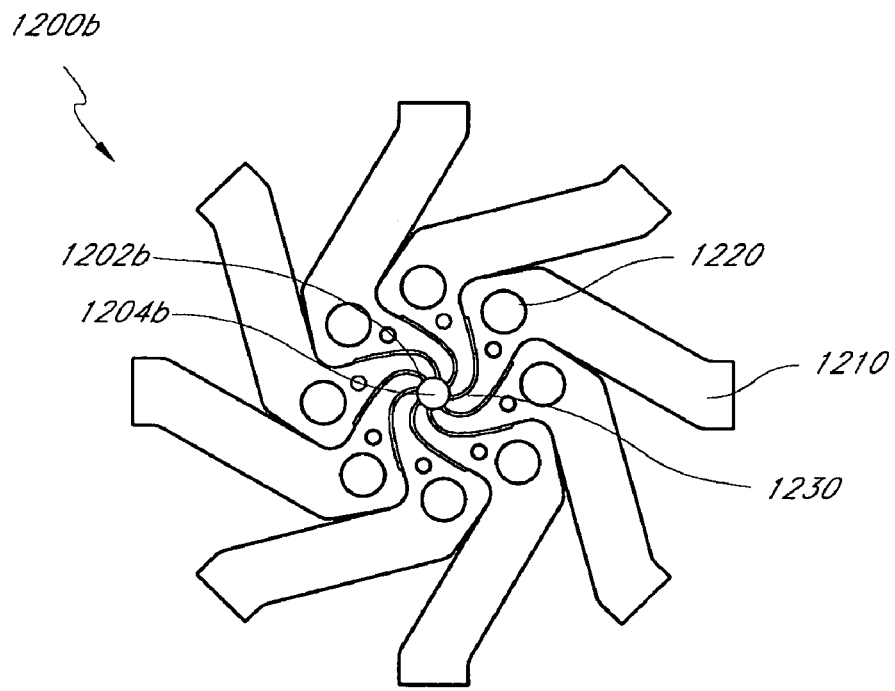
FIG. 12B is a front elevational view of an eight blade configuration shown in a closed position creating eight folds in a balloon catheter.

FIG. 12A illustrates an eight blade embodiment with the blades in an open position 1200a. Similar to the previously described embodiments, each blade has a body portion 1210, a profiled tip portion 1230, and an opening 1220 in the body portion 1210 of the blade. FIG. 12B shows the eight blade embodiment in a closed position 1200b so as to create eight folds in a balloon catheter.

Similar to the embodiments described above, the eight blade embodiment has blades having profiled tips 1230 having at least partially concave surfaces so as to substantially mate with partially convex surfaces of the body portions 1210 leaving eight slight gaps for housing eight flutes during the balloon catheter folding process. In addition, the eight blade embodiment preferably has a body portion 1210 that has a V-like configuration so as to permit the eight blades to translate simultaneously radially inward without having any particular blade interfere with such uniform radial movement.

Configurations of the eight blade embodiment are more limited than, for example, the three blade embodiment because there is less open space between adjacent blades in the eight blade embodiment. As a result, an eight blade embodiment having blades with a substantially straight body portion 1210 would not permit the blades to translate radially inward so as to flute a balloon catheter because the blades would prematurely contact each other and prevent radial translation. However, it should be noted that the eight blade configuration is not limited to the specific V-like configuration as shown in FIGS. 12A and 12B and may include profiled blades of a variety of sizes and shapes so as to be capable of receiving a variety of sizes and shapes of balloon catheters and catheter shafts.

Figure 13A:
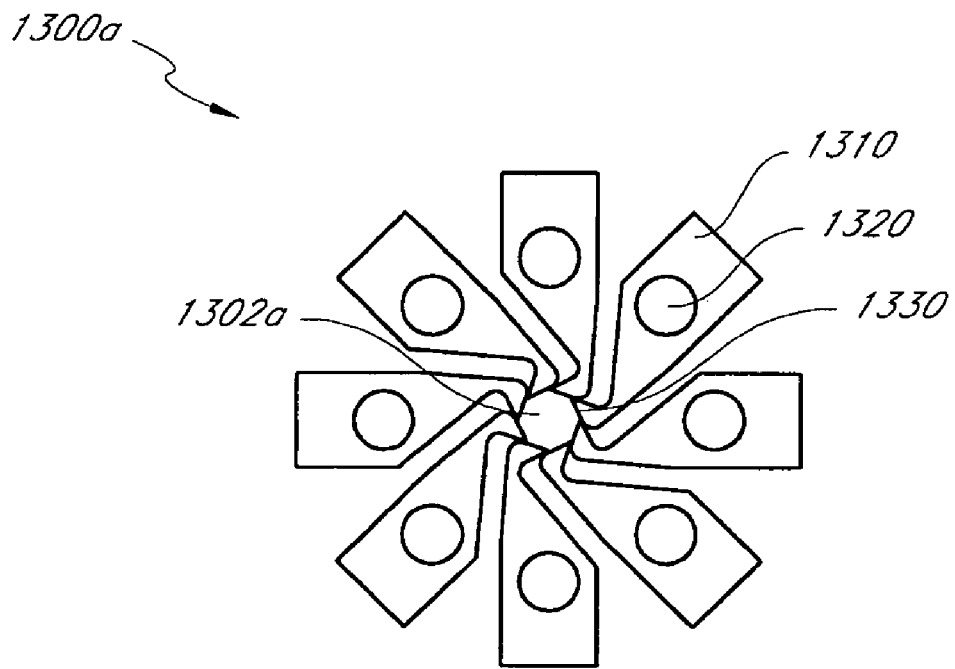
FIG. 13A is a front elevational view of an exemplary eight blade configuration shown in an open position of the balloon wrapping device as shown in FIG. 2.
Figure 13B:
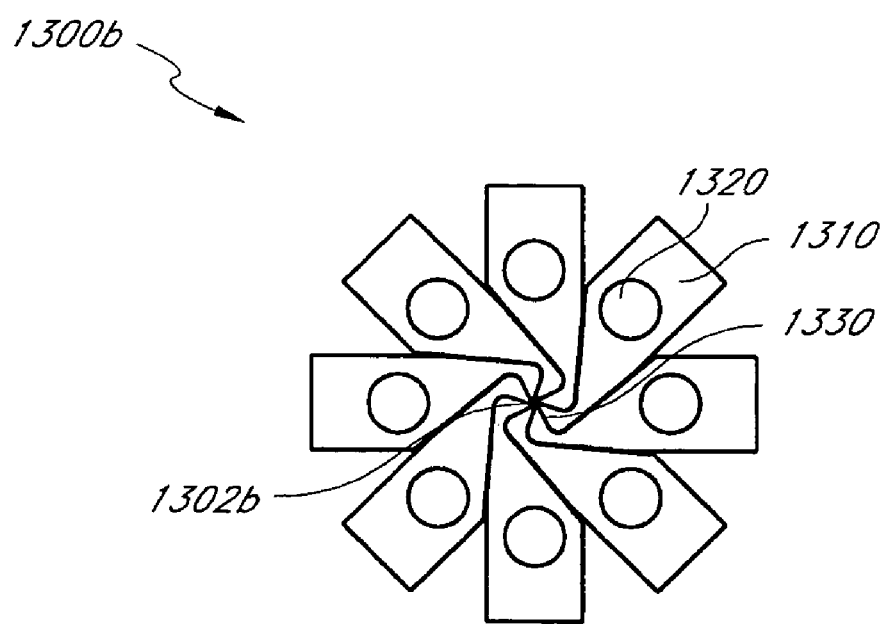
FIG. 13B is a front elevational view of an exemplary eight blade configuration shown in a closed position of the balloon wrapping device as shown in FIG. 2.

The blades of an exemplary balloon wrapping device will now be described in connection with FIGS. 13 and 14. With reference to FIGS. 13A and 13B, an end view of a balloon wrapping fixture incorporating a set of eight blades is shown. In FIG. 13A, the blades are in the retracted (i.e., open) position 1300a for receiving a folded balloon. FIG. 13B illustrates the set of blades of in the extended (i.e., closed) position 1300b. It should be noted that in one embodiment of the balloon wrapping device, a stent can be crimped onto the exterior of the balloon.

As shown in FIG. 13A, the embodiment comprises a device having eight profiled blades. For a balloon wrapping fixture, eight profiled blades are preferable because such a configuration has been found to be capable of sufficiently wrapping a fluted balloon catheter about a catheter shaft. Having less than eight profiled blades increases the possibility that gaps may be left in the wrapped balloon since the tips of three blades, for example, might not be capable of substantially wrapping a folded balloon about a round catheter shaft. Having more than eight profiled blades could be advantageous since such a system would likely create an opening closer to a round opening for wrapping a folded balloon about a round catheter shaft. However, as the number of blades increases, there is a greater possibility that adjacent blades will contact each other and interfere with inward radial translation of the set of blades. As a result, an eight blade configuration provides a balloon wrapping device with a proper balance between having an opening that will conform to a round balloon catheter shaft and minimizing interference of adjacent blades so as to permit uniform inward radially translation.

Each of the blades includes a body portion 1310, an opening 1320, and a profiled tip 1330. The tip geometry of the profiled tips 1330 allows for progressive reduction of the cavity diameter when the blades move radially inward toward the center of the cavity. As a result, when in an open position 1302a, the blades receive a folded balloon catheter. In this configuration, the plurality of blade tips 1330 substantially forms an octagon. As the blades move radially inward, the octagonal opening 1302a becomes progressively smaller. When in a closed position 1302b, the blades wrap a folded balloon catheter around a catheter shaft so as to minimize the diameter of the balloon catheter. In a closed position 1302b, the plurality of blade tips 1330 substantially form a circle that wraps the folded balloon catheter around a circular catheter shaft.

Each of the profiled blades preferably moves radially inward along a linear track during the wrapping process. More particularly, the blades may be attached to ball bearing slides that provide precision guidance with little or no play. Stepper motors are preferably provided for precisely controlling the movement of the blades. The stepper motors preferably control ball screws which are capable of controlling the position of the blades to within 0.001 inches (0.025 mm). The stepper motors may use optical sensors for improved alignment. Advantageously, the balloon can be wrapped with high consistency and uniformity in less than five seconds. It will be appreciated by those skilled in the art that the present balloon wrapping fixture provides a substantial improvement over existing wrapping fixtures which use relatively complex and expensive pivoting blade mechanisms.

Preferably, the balloon folding fixture is equipped with heated blades. Using heated blades, the folded balloon is heat-set and a vacuum is applied to lock the folds in place. As shown in FIGS. 13A and 13B, each blade may be formed with an opening 1320 or other receptacle for receiving a heating unit. In another embodiment, the opening 1320 itself may comprise a heating element for heating the profiled blades of the balloon wrapping device.

The size and shape of the profiled blades varies among embodiments. In one embodiment, the balloon wrapping fixture receives a small folded balloon catheter. In such embodiment, the profiled blades can open to a maximum diameter of approximately 0.1884 inches and can close to a minimum diameter of approximately 0.0300 inches. In another embodiment, the profiled blades can receive a medium-sized balloon catheter such that the blades can open to a maximum diameter of approximately 0.2637 inches and can close to a minimum diameter of approximately 0.0400 inches. In yet another embodiment, the profiled blades of the balloon wrapping device can receive a large folded balloon catheter. In this embodiment, the blades retract to an open position having a maximum diameter of approximately 0.3761 inches and close to a closed position having a minimum diameter of approximately 0.0400 inches.

Figure 14A:
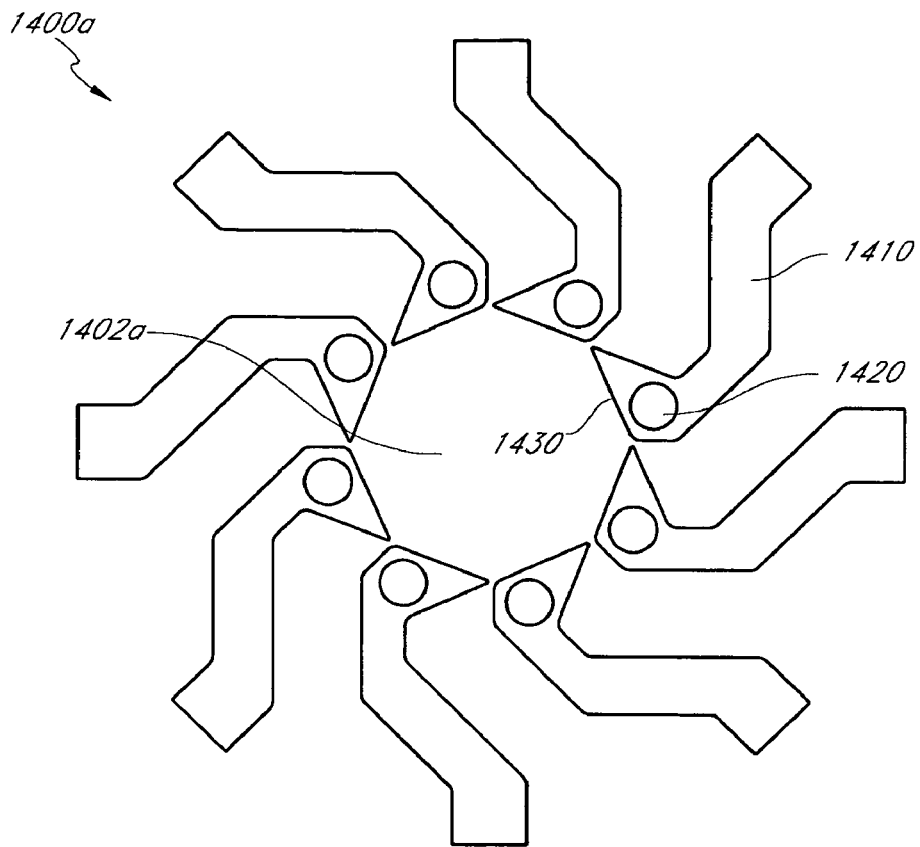
FIG. 14A is a front elevational view of an offset eight blade configuration shown in an open position of the balloon wrapping device as shown in FIG. 2.
Figure 14B:
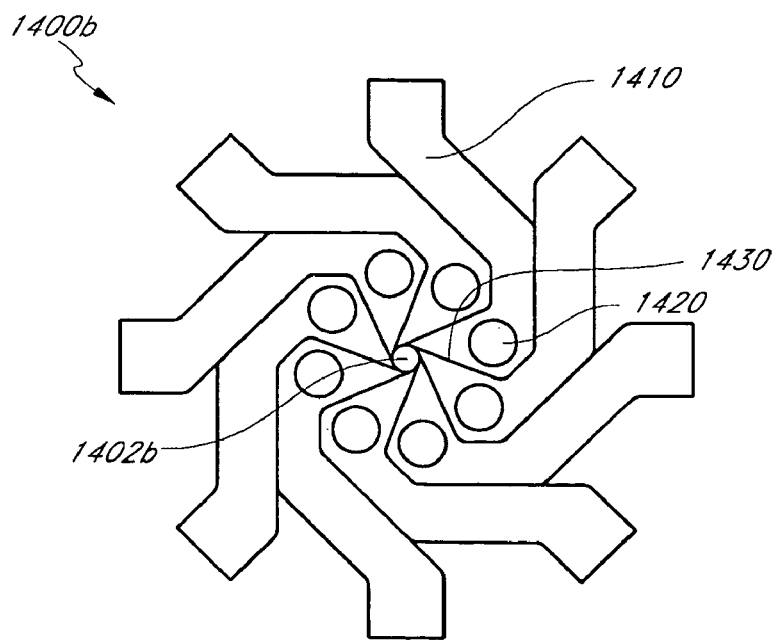
FIG. 14B is a front elevational view of an offset eight blade configuration shown in a closed position of the balloon wrapping device as shown in FIG. 2.

FIGS. 14A and 14B show an eight blade configuration for a balloon wrapping device, wherein such blades have an offset in their body so as to permit the blades to sufficiently interlock with each other when in the closed position 1400b. In FIG. 14A, the blades are in the retracted (i.e., open) position 1400a for receiving a folded balloon. FIG. 14B illustrates the set of blades of in the extended (i.e., closed) position 1400b. It should be noted that a stent can be crimped onto the exterior of the balloon.

The body portion 1410 of the blade in FIGS. 14A and 14B includes an angled offset so that adjacent blades can sufficiently mate with each other when the eight blades are translated radially inward. Such embodiment provides an alternative embodiment to the straight bodied blades shown in FIGS. 13A and 13B. Similar to the wrapping blades shown in FIGS. 13A and 13B, the wrapping blades shown in FIGS. 14A and 14B have profiled tips 1430 with a substantially flat configuration. As a result, the tip geometry of the profiled tips 1430 allows for progressive reduction of the cavity diameter when the blades move radially inward toward the center of the cavity.

When in an open position 1400a, the blades receive a folded balloon catheter. In this configuration, the plurality of blade tips 1430 substantially forms an octagon. As the blades move radially inward, the octagonal opening 1402a becomes progressively smaller. When in a closed position 1400b, the blades wrap a folded balloon catheter around a catheter shaft so as to minimize the diameter of the balloon catheter. In a closed position 1400b, the plurality of blade tips 1430 substantially form a circle that wraps the folded balloon catheter around a circular catheter shaft.

Preferably, the balloon folding fixture having offset blades is equipped with heated blades. As shown in FIGS. 14A and 14B, each blade may be formed with an opening 1420 or other receptacle for receiving a heating unit. In another embodiment, the opening 1420 itself may comprise a heating element for heating the profiled blades of the balloon wrapping device.

The above presents a description of the best mode contemplated for carrying out the present balloon folding and wrapping devices and methods, and of the manner and process of making and using them, in such full, clear, concise, and exact terms as to enable any person skilled in the art to which it pertains to make and use these devices and methods. These balloon folding and wrapping devices and methods are, however, susceptible to modifications and alternative method steps from those discussed above that are fully equivalent. Consequently, these balloon folding and wrapping devices and methods are not limited to the particular embodiments disclosed. On the contrary, these balloon folding and wrapping devices and methods cover all modifications and alternative constructions and methods coming within the spirit and scope of the present invention.

What is claimed is:

1. A balloon folding apparatus, comprising:
   a base unit;
   a control unit coupled to the base unit;
   a power source;
   a plurality of arms coupled to the base unit and configured in a radial pattern converging toward a central axis, wherein the plurality of arms is capable of translating in a radial direction;
   a plurality of motors coupled to the power source for enabling the plurality of arms to translate in a radial direction;
   a plurality of blades capable of being attached to and detached from the plurality of arms, wherein the plurality of blades is capable of translating in a radial direction and engaging a balloon catheter during the folding process;
   a cavity defined by the convergence of the plurality of blades about the central axis, wherein the cavity is capable of receiving a balloon catheter;

a carriage coupled to the base unit and disposed substantially near the central axis, wherein the carriage is capable of translating in a direction generally parallel to the central axis; and a mounting unit coupled to the carriage, wherein the mounting unit is capable of holding a balloon catheter and providing the balloon catheter to the cavity for engagement by the plurality of blades.

2. The balloon folding apparatus of claim 1, wherein the control unit is capable of controlling the inflation of the balloon catheter.

3. The balloon folding apparatus of claim 1, wherein the control unit further comprises a pump for applying a vacuum to the interior of the balloon catheter which facilitates holding the shape of the balloon catheter after the folding process.

4. The balloon folding apparatus of claim 1 further comprising a plurality of receiving rods disposed at least partially on the plurality of arms.

5. The balloon folding apparatus of claim 4 further comprising a plurality of cylindrical cavities disposed on the plurality of blades for attaching the plurality of blades to the plurality of receiving rods.

6. The balloon folding apparatus of claim 1, wherein the plurality of motors comprises a plurality of stepper motors for providing precise radial movement of the plurality of arms.

7. The balloon folding apparatus of claim 1, wherein each of the plurality of blades is mounted to linear guides comprising ball bearings.

8. The balloon folding apparatus of claim 1, wherein each of the plurality of blades is composed of heat treated beryllium copper.

9. The balloon folding apparatus of claim 1, wherein each of the plurality of blades has an integrated electric heater.

10. The balloon folding apparatus of claim 1, wherein each of the plurality of blades has an integrated thermocouple.

11. The balloon folding apparatus of claim 1, wherein the plurality of blades comprises three blades.

12. The balloon folding apparatus of claim 1, wherein the plurality of blades comprises four blades.

13. The balloon folding apparatus of claim 1, wherein the plurality of blades comprises five blades.

14. The balloon folding apparatus of claim 1, wherein the plurality of blades comprises six blades.

15. The balloon folding apparatus of claim 1, wherein the plurality of blades comprises eight blades.

16. A balloon wrapping apparatus, comprising:
a base unit;
a control unit coupled to the base unit;
a power source;
a plurality of arms coupled to the base unit and configured in a radial pattern converging toward a central axis, wherein the plurality of arms is capable of translating in a radial direction;
a plurality of motors coupled to the power source for enabling the plurality of arms to translate in a radial direction;
a plurality of blades capable of being attached to and detached from the plurality of arms, wherein the plurality of blades is capable of translating in a radial direction and engaging a balloon catheter during the wrapping process;
a cavity defined by the convergence of the plurality of blades about the central axis, wherein the cavity is capable of receiving a balloon catheter;
a carriage coupled to the base unit and disposed substantially near the central axis, wherein the carriage is capable of translating in a direction generally parallel to the central axis; and
a mounting unit coupled to the carriage, wherein the mounting unit is capable of holding a balloon catheter and providing the balloon catheter to the cavity for engagement by the plurality of blades.

17. The balloon wrapping apparatus of claim 16, wherein the control unit further comprises a pump for applying a vacuum to the interior of the balloon catheter which facilitates holding the shape of the balloon catheter after the wrapping process.

18. The balloon wrapping apparatus of claim 16 further comprising a plurality of receiving rods disposed at least partially on the plurality of arms.

19. The balloon wrapping apparatus of claim 18 further comprising a plurality of cylindrical cavities disposed on the plurality of blades for attaching the plurality of blades to the plurality of receiving rods.

20. The balloon wrapping apparatus of claim 16, wherein the plurality of motors comprises a plurality of stepper motors for providing precise radial movement of the plurality of arms.

21. The balloon wrapping apparatus of claim 16, wherein each of the plurality of blades is mounted to linear guides comprising ball bearings.

22. The balloon wrapping apparatus of claim 16, wherein each of the plurality of blades is composed of heat treated beryllium copper.

23. The balloon wrapping apparatus of claim 16, wherein each of the plurality of blades has an integrated electric heater.

24. The balloon wrapping apparatus of claim 16, wherein each of the plurality of blades has an integrated thermocouple.

25. The balloon wrapping apparatus of claim 16, wherein the plurality of blades comprises three blades.

26. The balloon wrapping apparatus of claim 16, wherein the plurality of blades comprises four blades.

27. The balloon wrapping apparatus of claim 16, wherein the plurality of blades comprises five blades.

28. The balloon wrapping apparatus of claim 16, wherein the plurality of blades comprises six blades.

29. The balloon wrapping apparatus of claim 16, wherein the plurality of blades comprises eight blades.

* * * * *